(12) United States Patent
He et al.

(10) Patent No.: US 8,486,961 B2
(45) Date of Patent: Jul. 16, 2013

(54) PYRROLO[4,3,2-DE]QUINOLIN-8-AMINE COMPOUNDS AND METHODS OF THEIR PREPARATION AND USE

(75) Inventors: Min He, Congers, NY (US); Jeffrey Edwin Janso, Montclair, NJ (US); Ker Yu, Pine Brook, NJ (US); Leonard Alexander McDonald, Mountainside, NJ (US); Laurel Rita Barbieri, Blauvelt, NY (US); Ariamala Gopalsamy, Mahwah, NJ (US)

(73) Assignee: Wyeth LLC, Madison, NJ (US)

( * ) Notice: Subject to any disclaimer, the term of this patent is extended or adjusted under 35 U.S.C. 154(b) by 585 days.

(21) Appl. No.: 12/539,869

(22) Filed: Aug. 12, 2009

(65) Prior Publication Data
US 2010/0041692 A1     Feb. 18, 2010

Related U.S. Application Data

(60) Provisional application No. 61/088,192, filed on Aug. 12, 2008, provisional application No. 61/122,449, filed on Dec. 15, 2008.

(51) Int. Cl.
*A61K 31/437* (2006.01)
*C07D 471/06* (2006.01)

(52) U.S. Cl.
USPC .............................. 514/292; 546/87

(58) Field of Classification Search
None
See application file for complete search history.

(56) References Cited

U.S. PATENT DOCUMENTS 4,959,370 A      9/1990 Crews et al.
5,843,955 A *   12/1998 Tamaoki et al. ............. 514/292
6,815,449 B2 * 11/2004 Akama et al. ................ 514/292

FOREIGN PATENT DOCUMENTS
WO    WO 2009/006319 A2 *  1/2009

OTHER PUBLICATIONS

Kasai, S. et al. The first total synthesis of lymphostin. Tetrahedron Letters. 2004, vol. 45, p. 2847, scheme 2.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Wander S. A., Hennessy, B. T., Slingerland, J. M. Next-generation mTOR inhibitors in clinical oncology: how pathway complexity informs therapeutic strategy. The Journal of Clinical Investigation, 2011, 121, 1231-1241.*

* cited by examiner

*Primary Examiner* — Jason M Nolan
*Assistant Examiner* — Po-Chih Chen
(74) *Attorney, Agent, or Firm* — David Rubin

(57) ABSTRACT

The present invention relates to compounds of formula I:

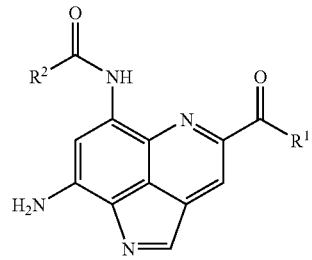

methods of their use, processes for their preparation and isolated actinomycetes strains capable of preparing pyrrolo [4,3,2-de]quinolin-8-amine compounds.

3 Claims, 6 Drawing Sheets

FIG. 1A

CTCAGGACGAACGCTGGCGGCGTGCTTAACACATGCAAGTCGAGCGGAAAGGCCCTTCGGGGTACTCGAGCGGCGAACGG
GTGAGTAACACGTGAGTAACCTGCCCTAGGCTTTGGGATAACCCCGGGAAACCGGGGCTAATACCGAATATGACTGGCTG
CCGCATGGTGGTTGGTGGAAAGATTTTTCGGCTTGGGATGGACTCGCGGCCTATCAGCTTGTTGGTGGGGTAATGGCCTA
CCAAGGCGGCGACGGGTAGCCGGCCTGAGAGGGCGACCGGCCACACTGGGACTGAGACACGGCCCAGACTCCTACGGGAG
GCAGCAGTGGGGAATCTTGCACAATGGGCGGAAGCCTGATGCAGCGACGCCGCGTGAGGGATGACGGCCTTCGGGTTGTA
AACCTCTTTCAGCAGGGACGAAGCGTTTGTGACGGTACCTGCAGAAGAAGCGCCGGCCAACTACGTGCCAGCAGCCGCGG
TAAGACGTAGGGCGCAAGCGTTGTCCGGATTTATTGGGCGTAAAGAGCTCGTAGGCGGCTTGTCGCGTCGACTGTGAAAA
CCCGTGGCTCAACTGCGGGCTTGCAGTCGATACGGGCAGGCTAGAGTTCGGTAGGGGAGACTGGAATTCCTGGTGTAGCG
GTGAAATGCGCAGATATCAGGAGGAACACCGGTGGCGAAGGCGGGTCTCTGGGCCGATACTGACGCTGAGGAGCGAAAGC
GTGGGGAGCGAACAGGATTAGATACCCTGGTAGTCCACGCTGTAAACGTTGGGCGCTAGGTGTGGGGGCCTCTCCGGTT
CTCTGTGCCGCAGCTAACGCATTAAGCGCCCCGCCTGGGGAGTACGGCCGCAAGGCTAAAACTCAAAGGAATTGACGGGG
GCCCGCACAAGCGGCGGAGCATGCGGATTAATTCGATGCAACGCGAAGAACCTTACCTGGGTTTGACATCGCCGGAAATC
CTTCAGAGATGGGGGGTCCTTCGGGGCCGGTGACAGGTGGTGCATGGCTGTCGTCAGCTCGTGTCGTGAGATGTTGGGTT
AAGTCCCGCAACGAGCGCAACCCTTGTTCGATGTTGCCAGCGCGTTATGGCGGGGACTCATCGAAGACTGCCGGGGTCAA
CTCGGAGGAAGGTGGGGATGACGTCAAGTCATCATGCCCCTTATGTCCAGGGCTTCACGCATGCTACAATGGCCGGTACA
ATGGGCTGCGATACCGTGAGGTGGAGCGAATCCCAAAAAGCCGGTCTCAGTTCGGATCGGGGTCTGCAACTCGACCCCGT
GAAGTCGGAGTCGCTAGTAATCGCAGATCAGCAACGCTGCGGTGAATACGTTCCCGGGCCTTGTACACACCGCCCGTCAC
GTCACGAAAGTCGGCAACACCCGAAGCCGGTGGCCTAACCCTTGTGGGGGAGCCGTCGAAGGTGGGGCTGGCGATTGGG
ACGAAGTCG (SEQ ID NO:1)

FIG. 1B

GCTCAGGACGAACGCTGGCGGCGTGCTTAACACATGCAAGTCGAGCGGAAAGGCCCTTCGGGGTACTCGAGCGGCGAAC
GGGTGAGTAACACGTGAGTAACCTGCCCCAGGCTTTGGGATAACCCCGGGAAACCGGGGCTAATACCGAATATTACCGG
CTGCCGCATGGCGGTTGGTGGAAAGTTTTTCGGCTTGGGATGGACTCGCGGCCTATCAGCTTGTTGGTGGGGTAATGGC
CTACCAAGGCGGCGACGGGTAGCCGGCCTGAGAGGGCGACCGGCCACACTGGGACTGAGACACGGCCCAGACTCCTACG
GGAGGCAGCAGTGGGGAATCTTGCACAATGGGCGGAAGCCTGATGCAGCGACGCCGCGTGAGGGATGACGGCCTTCGGG
TTGTAAACCTCTTTCAGCAGGGACGAAGCGTTTGTGACGGTACCTGCAGAAGAAGCGCCGGCCAACTACGTGCCAGCAG
CCGCGGTAAGACGTAGGGCGCAAGCGTTGTCCGGATTTATTGGGCGTAAAGAGCTCGTAGGCGGCTTGTCGCGTCGACT
GTGAAAACCCGTGGCTCAACTGCGGGCTTGCAGTCGATACGGGCAGGCTAGAGTTCGGTAGGGGAGACTGGAATTCCTG
GTGTAGCGGTGAAATGCGCAGATATCAGGAGGAACACCGGTGGCGAAGGCGGGTCTCTGGGCCGATACTGACGCTGAGG
AGCGAAAGCGTGGGGAGCGAACAGGATTAGATACCCTGGTAGTCCACGCTGTAAACGTTGGGCGCTAGGTGTGGGGGGC
CTCTCCGGTTCTCTGTGCCGCAGCTAACGCATTAAGCGCCCCGCCTGGGGAGTACGGCCGCAAGGCTAAAACTCAAAGG
AATTGACGGGGGCCCGCACAAGCGGCGGAGCATGCGGATTAATTCGATGCAACGCGAAGAACCTTACCTGGGTTTGACA
TCGCCGGAAATCCTTCAGAGATGGGGGGTCCTTCGGGGCCGGTGACAGGTGGTGCATGGCTGTCGTCAGCTCGTGTCGT
GAGATGTTGGGTTAAGTCCCGCAACGAGCGCAACCCTTGTTCGATGTTGCCAGCGCGTTATGGCGGGGACTCATCGAAG
ACTGCCGGGGTCAACTCGGAGGAAGGTGGGGATGACGTCAAGTCATCATGCCCCTTATGTCCAGGGCTTCACGCATGCT
ACAATGGCCGGTACAATGGGCTGCGATACCGTGAGGTGGAGCGAATCCCAAAAAGCCGGTCTCAGTTCGGATCGGGGTC
TGCAACTCGACCCCGTGAAGTCGGAGTCGCTAGTAATCGCAGATCAGCAACGCTGCGGTGAATACGTTCCCGGGCCTTG
TACACACCGCCCGTCACGTCACGAAAGTCGGCAACACCCGAAGCCGGTGGCCTAACCCTTGTGGGGGAGCCGTCGAAG
GTGGGGCTGGCGATTGGGACGAAGT (SEQ ID NO:2)

FIG. 1C

CGGTTGGTGGAAAGTTTTTC (SEQ ID NO:3)

FIG. 3A

```
                1                                                                    50
S.arenicola     AGAGTTTGAT CCTGGCTCAG GACGAACGCT GGCGGCGTGC TTAACACATG
S.tropica       AGAGTTTGAT CCTGGCTCAG GACGAACGCT GGCGGCGTGC TTAACACATG
DPJ-0019        AGAGTTTGAT CCTGGCTCAG GACGAACGCT GGCGGCGTGC TTAACACATG
DPJ-0024        AGAGTTTGAT CCTGGCTCAG GACGAACGCT GGCGGCGTGC TTAACACATG 51                                                                   100
S.arenicola     CAAGTCGAGC GGAAAGGCCC TTCGGGGTAC TCGAGCGGCG AACGGGTGAG
S.tropica       CAAGTCGAGC GGAAAGGCCC TTCGGGGTAC TCGAGCGGCG AACGGGTGAG
DPJ-0019        CAAGTCGAGC GGAAAGGCCC TTCGGGGTAC TCGAGCGGCG AACGGGTGAG
DPJ-0024        CAAGTCGAGC GGAAAGGCCC TTCGGGGTAC TCGAGCGGCG AACGGGTGAG 101                                                                  150
S.arenicola     TAACACGTGA GTAACCTGCC CCAGGCTTTG GGATAACCCC GGGAAACCGG
S.tropica       TAACACGTGA GTAACCTGCC CCAGGCTTTG GGATAACCCC GGGAAACCGG
DPJ-0019        TAACACGTGA GTAACCTGCC CTAGGCTTTG GGATAACCCC GGGAAACCGG
DPJ-0024        TAACACGTGA GTAACCTGCC CCAGGCTTTG GGATAACCCC GGGAAACCGG 151                                                                  200
S.arenicola     GGCTAATACC GGATATGACC ATCTGTCGCA TGGTGGGTGG TGGAAAGATT
S.tropica       GGCTAATACC GGATATGACT GGCTGCCGCA TGGTGGTTGG TGGAAAGATT
DPJ-0019        GGCTAATACC GAATATGACT GGCTGCCGCA TGGTGGTTGG TGGAAAGATT
DPJ-0024        GGCTAATACC GAATATTACC GGCTGCCGCA TGGCGGTTGG TGGAAAG TT
                                                                              →A198

201                                                                  250
S.arenicola     TTTTGGCTTG GGATGGGCTC GCGGCCTATC AGCTTGTTGG TGGGGTGATG
S.tropica       TTTTGGCTTG GGATGGGCTC GCGGCCTATC AGCTTGTTGG TGGGGTGATG
DPJ-0019        TTTCGGCTTG GGATGGACTC GCGGCCTATC AGCTTGTTGG TGGGGTAATG
DPJ-0024        TTTCGGCTTG GGATGGACTC GCGGCCTATC AGCTTGTTGG TGGGGTAATG 251                                                                  300
S.arenicola     GCCTACCAAG GCGGCGACGG GTAGCCGGCC TGAGAGGGCG ACCGGCCACA
S.tropica       GCCTACCAAG GCGGCGACGG GTAGCCGGCC TGAGAGGGCG ACCGGCCACA
DPJ-0019        GCCTACCAAG GCGGCGACGG GTAGCCGGCC TGAGAGGGCG ACCGGCCACA
DPJ-0024        GCCTACCAAG GCGGCGACGG GTAGCCGGCC TGAGAGGGCG ACCGGCCACA 301                                                                  350
S.arenicola     CTGGGACTGA GACACGGCCC AGACTCCTAC GGGAGGCAGC AGTGGGGAAT
S.tropica       CTGGGACTGA GACACGGCCC AGACTCCTAC GGGAGGCAGC AGTGGGGAAT
DPJ-0019        CTGGGACTGA GACACGGCCC AGACTCCTAC GGGAGGCAGC AGTGGGGAAT
DPJ-0024        CTGGGACTGA GACACGGCCC AGACTCCTAC GGGAGGCAGC AGTGGGGAAT C351                                                                 400
S.arenicola     CTTGCACAAT GGGCGGAAGC CTGATGCAGC GACGCCGCGT GAGGGATGAC
S.tropica       CTTGCACAAT GGGCGGAAGC CTGATGCAGC GACGCCGCGT GAGGGATGAC
DPJ-0019        CTTGCACAAT GGGCGGAAGC CTGATGCAGC GACGCCGCGT GAGGGATGAC
DPJ-0024        CTTGCACAAT GGGCGGAAGC CTGATGCAGC GACGCCGCGT GAGGGATGAC T442
                401                                                 T443  450
S.arenicola     GGCCTTCGGG TTGTAAACCT CTTTCAGCAG GGACGAAGCG TTTGTGACGG
S.tropica       GGCCTTCGGG TTGTAAACCT CTTTCAGCAG GGACGAAGCG TTTGTGACGG
DPJ-0019        GGCCTTCGGG TTGTAAACCT CTTTCAGCAG GGACGAAGCG TTTGTGACGG
DPJ-0024        GGCCTTCGGG TTGTAAACCT CTTTCAGCAG GGACGAAGCG TTTGTGACGG
```

FIG. 3B

```
            451                                                500
S.arenicola TACCTGCAGA AGAAGCGCCG GCCAACTACG TGCCAGCAGC CGCGGTAAGA
S.tropica   TACCTGCAGA AGAAGCGCCG GCCAACTACG TGCCAGCAGC CGCGGTAAGA
DPJ-0019    TACCTGCAGA AGAAGCGCCG GCCAACTACG TGCCAGCAGC CGCGGTAAGA
DPJ-0024    TACCTGCAGA AGAAGCGCCG GCCAACTACG TGCCAGCAGC CGCGGTAAGA 501                                                550
S.arenicola CGTAGGGCGC AAGCGTTGTC CGGATTTATT GGGCGTAAAG AGCTCGTAGG
S.tropica   CGTAGGGCGC AAGCGTTGTC CGGATTTATT GGGCGTAAAG AGCTCGTAGG
DPJ-0019    CGTAGGGCGC AAGCGTTGTC CGGATTTATT GGGCGTAAAG AGCTCGTAGG
DPJ-0024    CGTAGGGCGC GAGCGTTGTC CGGATTTATT GGGCGTAAAG AGCTCGTAGG 551                                                600
S.arenicola CGGCTTGTCG CGTCGACTGT GAAAACCCGT GGCTCAACTG CGGGCTTGCA
S.tropica   CGGCTTGTCG CGTCGACTGT GAAAACCCGT GGCTCAACTG CGGGCTTGCA
DPJ-0019    CGGCTTGTCG CGTCGACTGT GAAAACCCGT GGCTCAACTG CGGGCTTGCA
DPJ-0024    CGGCTTGTCG CGTCGACTGT GAAAACCCGT GGCTCAACTG CGGGCTTGCA 601                                                650
S.arenicola GTCGATACGG GCAGGCTAGA GTTCGGTAGG GGAGACTGGA ATTCCTGGTG
S.tropica   GTCGATACGG GCAGGCTAGA GTTCGGTAGG GGAGACTGGA ATTCCTGGTG
DPJ-0019    GTCGATACGG GCAGGCTAGA GTTCGGTAGG GGAGACTGGA ATTCCTGGTG
DPJ-0024    GTCGATACGG GCAGGCTAGA GTTCGGTAGG GGAGACTGGA ATTCCTGGTG 651                                                700
S.arenicola TAGCGGTGAA ATGCGCAGAT ATCAGGAGGA ACACCGGTGG CGAAGGCGGG
S.tropica   TAGCGGTGAA ATGCGCAGAT ATCAGGAGGA ACACCGGTGG CGAAGGCGGG
DPJ-0019    TAGCGGTGAA ATGCGCAGAT ATCAGGAGGA ACACCGGTGG CGAAGGCGGG
DPJ-0024    TAGCGGTGAA ATGCGCAGAT ATCAGGAGGA ACACCGGTGG CGAAGGCGGG 701                                                750
S.arenicola TCTCTGGGCC GATACTGACG CTGAGGAGCG AAAGCGTGGG GAGCGAACAG
S.tropica   TCTCTGGGCC GATACTGACG CTGAGGAGCG AAAGCGTGGG GAGCGAACAG
DPJ-0019    TCTCTGGGCC GATACTGACG CTGAGGAGCG AAAGCGTGGG GAGCGAACAG
DPJ-0024    TCTCTGGGCC GATACTGACG CTGAGGAGCG AAAGCGTGGG GAGCGAACAG 751                                                800
S.arenicola GATTAGATAC CCTGGTAGTC CACGCTGTAA ACGTTGGGCG CTAGGTGTGG
S.tropica   GATTAGATAC CCTGGTAGTC CACGCTGTAA ACGTTGGGCG CTAGGTGTGG
DPJ-0019    GATTAGATAC CCTGGTAGTC CACGCTGTAA ACGTTGGGCG CTAGGTGTGG
DPJ-0024    GATTAGATAC CCTGGTAGTC CACGCTGTAA ACGTTGGGCG CTAGGTGTGG 801                                                850
S.arenicola GGGGCCTCTC CGGTTCTCTG TGCCGCAGCT AACGCATTAA GCGCCCCGCC
S.tropica   GGAGCCTCTC CGGTTCTCTG TGCCGCAGCT AACGCATTAA GCGCCCCGCC
DPJ-0019    GGGGCCTCTC CGGTTCTCTG TGCCGCAGCT AACGCATTAA GCGCCCCGCC
DPJ-0024    GGGGCCTCTC CGGTTCTCTG TGCCGCAGCT AACGCATTAA GCGCCCCGCC 851                                                900
S.arenicola TGGGGAGTAC GGCCGCAAGG CTAAAACTCA AAGGAATTGA CGGGGGCCCG
S.tropica   TGGGGAGTAC GGCCGCAAGG CTAAAACTCA AAGGAATTGA CGGGGGCCCG
DPJ-0019    TGGGGAGTAC GGCCGCAAGG CTAAAACTCA AAGGAATTGA CGGGGGCCCG
DPJ-0024    TGGGGAGTAC GGCCGCAAGG CTAAAACTCA AAGGAATTGA CGGGGGCCCG
```

FIG. 3C

```
            901                                                      950
S.arenicola CACAAGCGGC GGAGCATGCG GATTAATTCG ATGCAACGCG AAGAACCTTA
S.tropica   CACAAGCGGC GGAGCATGCG GATTAATTCG ATGCAACGCG AAGAACCTTA
DPJ-0019    CACAAGCGGC GGAGCATGCG GATTAATTCG ATGCAACGCG AAGAACCTTA
DPJ-0024    CACAAGCGGC GGAGCATGCG GATTAATTCG ATGCAACGCG AAGAACCTTA 951                                                     1000
S.arenicola CCTGGGTTTG ACATCGCCGG AAATCCTTCA GAGATGGGGG GTCCTTCGGG
S.tropica   CCTGGGTTTG ACATCGCCGG AAATCCTTCA GAGATGGGGG GTCCTTCGGG
DPJ-0019    CCTGGGTTTG ACATCGCCGG AAATCCTTCA GAGATGGGGG GTCCTTCGGG
DPJ-0024    CCTGGGTTTG ACATCGCCGG AAATCCTTCA GAGATGGGGG GTCCTTCGGG 1001                                                    1050
S.arenicola GCCGGTGACA GGTGGTGCAT GGCTGTCGTC AGCTCGTGTC GTGAGATGTT
S.tropica   GCCGGTGACA GGTGGTGCAT GGCTGTCGTC AGCTCGTGTC GTGAGATGTT
DPJ-0019    GCCGGTGACA GGTGGTGCAT GGCTGTCGTC AGCTCGTGTC GTGAGATGTT
DPJ-0024    GCCGGTGACA GGTGGTGCAT GGCTGTCGTC AGCTCGTGTC GTGAGATGTT 1051                                                    1100
S.arenicola GGGTTAAGTC CCGCAACGAG CGCAACCCTT GTTCGATGTT GCCAGCGCGT
S.tropica   GGGTTAAGTC CCGCAACGAG CGCAACCCTT GTTCGATGTT GCCAGCGCGT
DPJ-0019    GGGTTAAGTC CCGCAACGAG CGCAACCCTT GTTCGATGTT GCCAGCGCGT
DPJ-0024    GGGTTAAGTC CCGCAACGAG CGCAACCCTT GTTCGATGTT GCCAGCGCGT 1101                                                    1150
S.arenicola TATGGCGGGG ACTCATCGAA GACTGCCGGG GTCAACTCGG AGGAAGGTGG
S.tropica   TATGGCGGGG ACTCATCGAA GACTGCCGGG GTCAACTCGG AGGAAGGTGG
DPJ-0019    TATGGCGGGG ACTCATCGAA GACTGCCGGG GTCAACTCGG AGGAAGGTGG
DPJ-0024    TATGGCGGGG ACTCATCGAA GACTGCCGGG GTCAACTCGG AGGAAGGTGG 1151                                                    1200
S.arenicola GGATGACGTC AAGTCATCAT GCCCCTTATG TCCAGGGCTT CACGCATGCT
S.tropica   GGATGACGTC AAGTCATCAT GCCCCTTATG TCCAGGGCTT CACGCATGCT
DPJ-0019    GGATGACGTC AAGTCATCAT GCCCCTTATG TCCAGGGCTT CACGCATGCT
DPJ-0024    GGATGACGTC AAGTCATCAT GCCCCTTATG TCCAGGGCTT CACGCATGCT 1201                                                    1250
S.arenicola ACAATGGCCG GTACAGTGGG CTGCGATACC GTGAGGTGGA GCGAATCCCA
S.tropica   ACAATGGCCG GTACAATGGG CTGCGATACC GTGAGGTGGA GCGAATCCCA
DPJ-0019    ACAATGGCCG GTACAATGGG CTGCGATACC GTGAGGTGGA GCGAATCCCA
DPJ-0024    ACAATGGCCG GTACAATGGG CTGCGATACC GTGAGGTGGA GCGAATCCCA 1251                                                    1300
S.arenicola AAAAGCCGGT CTCAGTTCGG ATCGGGGTCT GCAACTCGAC CCCGTGAAGT
S.tropica   AAAAGCCGGT CTCAGTTCGG ATCGGGGTCT GCAACTCGAC CCCGTGAAGT
DPJ-0019    AAAAGCCGGT CTCAGTTCGG ATCGGGGTCT GCAACTCGAC CCCGTGAAGT
DPJ-0024    AAAAGCCGGT CTCAGTTCGG ATCGGGGTCT GCAACTCGAC CCCGTGAAGT 1301                                                    1350
S.arenicola CGGAGTCGCT AGTAATCGCA GATCAGCAAC GCTGCGGTGA ATACGTTCCC
S.tropica   CGGAGTCGCT AGTAATCGCA GATCAGCAAC GCTGCGGTGA ATACGTTCCC
DPJ-0019    CGGAGTCGCT AGTAATCGCA GATCAGCAAC GCTGCGGTGA ATACGTTCCC
DPJ-0024    CGGAGTCGCT AGTAATCGCA GATCAGCAAC GCTGCGGTGA ATACGTTCCC
```

FIG. 3D

```
             1351                                                        1400
S.arenicola  GGGCCTTGTA CACACCGCCC GTCACGTCAC GAAAGTCGGC AACACCCGAA
S.tropica    GGGCCTTGTA CACACCGCCC GTCACGTCAC GAAAGTCGGC AACACCCGAA
DPJ-0019     GGGCCTTGTA CACACCGCCC GTCACGTCAC GAAAGTCGGC AACACCCGAA
DPJ-0024     GGGCCTTGTA CACACCGCCC GTCACGTCAC GAAAGTCGGC AACACCCGAA 1401                                                        1450
S.arenicola  GCCGGTGGCC TAACCCTTGT GGGGGGAGCC GTCGAAGGTG GGGCTGGCGA
S.tropica    GCCGGTGGCC TAACCCTTGT GGGGGGAGCC GTCGAAGGTG GGGCTGGCGA
DPJ-0019     GCCGGTGGCC TAACCCTTGT GGGGGGAGCC GTCGAAGGTG GGGCTGGCGA
DPJ-0024     GCCGGTGGCC TAACCCTTGT GGGGGGAGCC GTCGAAGGTG GGGCTGGCGA 1451                            1479
S.arenicola  TTGGGACGAA GTCGTAACAA GGTAGCCGT  (SEQ ID NO:6)
S.tropica    TTGGGACGAA GTCGTAACAA GGTAGCCGT  (SEQ ID NO:7)
DPJ-0019     TTGGGACGAA GTCG......  .........  (SEQ ID NO:1)
DPJ-0024     TTGGGACGAA GT........  .........  (SEQ ID NO:2)
```

PYRROLO[4,3,2-DE]QUINOLIN-8-AMINE COMPOUNDS AND METHODS OF THEIR PREPARATION AND USE

CROSS REFERENCE TO RELATED APPLICATIONS

This application claims the benefit under 35 U.S.C. §119(e) to U.S. provisional applications 61/088,192, filed Aug. 12, 2008 and 61/122,449, filed Dec. 15, 2008, which are hereby incorporated by reference in their entirety.

FIELD OF THE INVENTION

The present invention relates to pyrrolo[4,3,2-de]quinolin-8-amine compounds and methods of their use and preparation. The invention also relates to isolated actinomycetes species capable of producing the pyrrolo[4,3,2-de]quinolin-8-amine compounds.

BACKGROUND OF THE INVENTION

Polycyclic aromatic alkaloids derived from marine plants and animals have been shown to exhibit a variety of biological activities. For example, plakinidines, which are pentacyclic pyrroloacridine compounds, are derived from the Vanuatuan red sponge, Plakortis, and have been shown to have antihelmintic activity in animals (U.S. Pat. No. 4,959,370).

Lymphostin is a pyrrolo[4,3,2-de]quinolin-8-amine produced by a soil bacterium which belongs to the genus Streptomyces and is suggested to have immunosuppressive activity (U.S. Pat. Nos. 5,843,955 and 6,815,449). Lymphostin has the following structure:

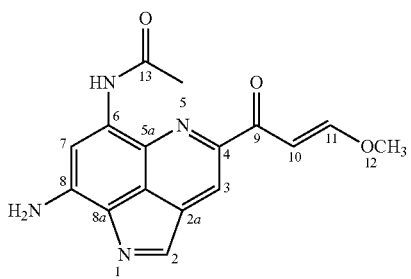 [SMILES: CO/C=C/C(=O)c1cc2c3c(c(N)cc(NC(C)=O)c3n1)N=C2]

U.S. Pat. No. 6,815,449 describes synthetic analogs derived from lymphostin, the majority of which are modified at the 4-position of the molecule. The only variation at the 6-position of lymphostin resulted in nearly ten-fold reduction in lymphocyte inhibitory activity (compare Compound no. 1 with 27 in table 3 of U.S. Pat. No. 6,815,449).

Applicants have developed novel pyrrolo[4,3,2-de]quinolin-8-amine compounds that surprisingly show potent inhibitory activity of mTOR, a serine/threonine kinase that regulates cell growth, cell proliferation, cell motility, cell survival, protein synthesis, and transcription and is thus implicated in various cancer pathways.

SUMMARY OF THE INVENTION

The present invention provides novel pyrrolo[4,3,2-de]quinolin-8-amine compounds for use in treatment of diseases associated with abnormal cellular proliferation, such as cancer.

One aspect of the invention provides a pyrrolo[4,3,2-de]quinolin-8-amine compound of formula I:

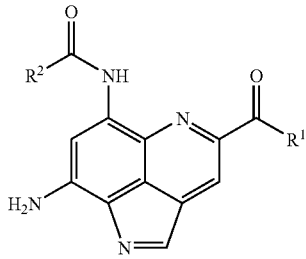

wherein,
$R^1$ is CH=CH—OCH$_3$ or (CH$_2$)$_2$OH; and
$R^2$ is $C_1$-$C_4$ alkyl; or
a tautomer thereof; a stereoisomer thereof; or a pharmaceutically acceptable salt of such compound, stereoisomer or tautomer;
provided that if $R^2$ is methyl, then $R^1$ is (CH$_2$)$_2$OH.

Another aspect of the invention provides a pharmaceutical composition comprising a compound of formula I or a tautomer, stereoisomer or pharmaceutically acceptable salt of such compound, stereoisomer or tautomer and a pharmaceutically acceptable carrier.

Another aspect of the invention provides a composition comprising an isolated compound of formula I, or a tautomer thereof; a stereoisomer thereof; or a pharmaceutically acceptable salt of such compound, stereoisomer or tautomer.

Another aspect of the invention provides an isolated actinomycetes strain having Deposit No. NRRL 50168 or NRRL 50167.

Another aspect of the invention provides an isolated pyrrolo[4,3,2-de]quinolin-8-amine compound, a tautomer of the compound, or a pharmaceutically acceptable salt of the compound or tautomer, wherein the compound is produced by an actinomycetes strain having Deposit No. NRRL 50168 or NRRL 50167;
provided that the compound is not lymphostin.

Another aspect of the invention provides (a) a process for the preparation of a pyrrolo[4,3,2-de]quinolin-8-amine compound; or (b) a pyrrolo[4,3,2-de]quinolin-8-amine compound or a tautomer, stereoisomer or pharmaceutically acceptable salt of such compound, stereoisomer or tautomer, provided that the compound is not lymphostin, prepared by a process, comprising:
fermenting an actinomycetes strain having Deposit No. NRRL 50168 or NRRL 50167 in a growth medium comprising a salt to form a fermented solution, wherein the pyrrolo[4,3,2-de]quinolin-8-amine compound is formed in the fermented solution; and
optionally purifying the pyrrolo[4,3,2-de]quinolin-8-amine compound.

Another aspect of the invention provides a compound selected from the group consisting of
(E)-N-(8-amino-4-(3-methoxyacryloyl)pyrrolo[4,3,2-de]quinolin-6-yl)-propionamide;
(E)-N-(8-amino-4-(3-methoxyacryloyl)pyrrolo[4,3,2-de]quinolin-6-yl)isobutyramide;
(E)-N-(8-amino-4-(3-methoxyacryloyl)pyrrolo[4,3,2-de]quinolin-6-yl)-3-methylbutanamide;
(E)-N-(8-amino-4-(3-methoxyacryloyl)pyrrolo[4,3,2-de]quinolin-6-yl)-2-methylbutanamide;

N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)acetamide; or
a tautomer thereof; a stereoisomer thereof; or a pharmaceutically acceptable salt of such compound, stereoisomer or tautomer.

Another aspect of the invention provides a method of inhibiting or treating a patient suffering from a disease associated with mTOR, particularly cancer.

Another aspect of the invention provides an isolated actinomycetes strain having Deposit No. NRRL 50168 or NRRL 50167. The invention also provides compounds and compositions produced by said strains and processes for the preparation of the compounds of formula I.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A depicts the nearly complete polynucleotide DNA sequence for the 16S rRNA gene of actinomycete strain DPJ-0019 (Deposit No. NRRL 50168) (SEQ ID NO:1).

FIG. 1B depicts the nearly complete polynucleotide DNA sequence for the 16S rRNA gene of DPJ-0024 (Deposit No. NRRL 50167) (SEQ ID NO:2).

FIG. 1C depicts a conserved DNA sequence in the 16S rRNA gene of DPJ-0024 (SEQ ID NO:3), which is not present in *Salinispora arenicola* or *Salinispora tropica* rRNA 16S rRNA gene sequences.

FIG. 3 is an alignment comparing the polynucleotide DNA sequences of 16S rRNA genes from *Salinispora* spp. *S. arenicola* (SEQ ID NO: 6) and *S. tropica* (SEQ ID NO:7) with DPJ-0024 (SEQ ID NO:2) and DPJ-0019 (SEQ ID NO:1).

DETAILED DESCRIPTION

Figure 2:
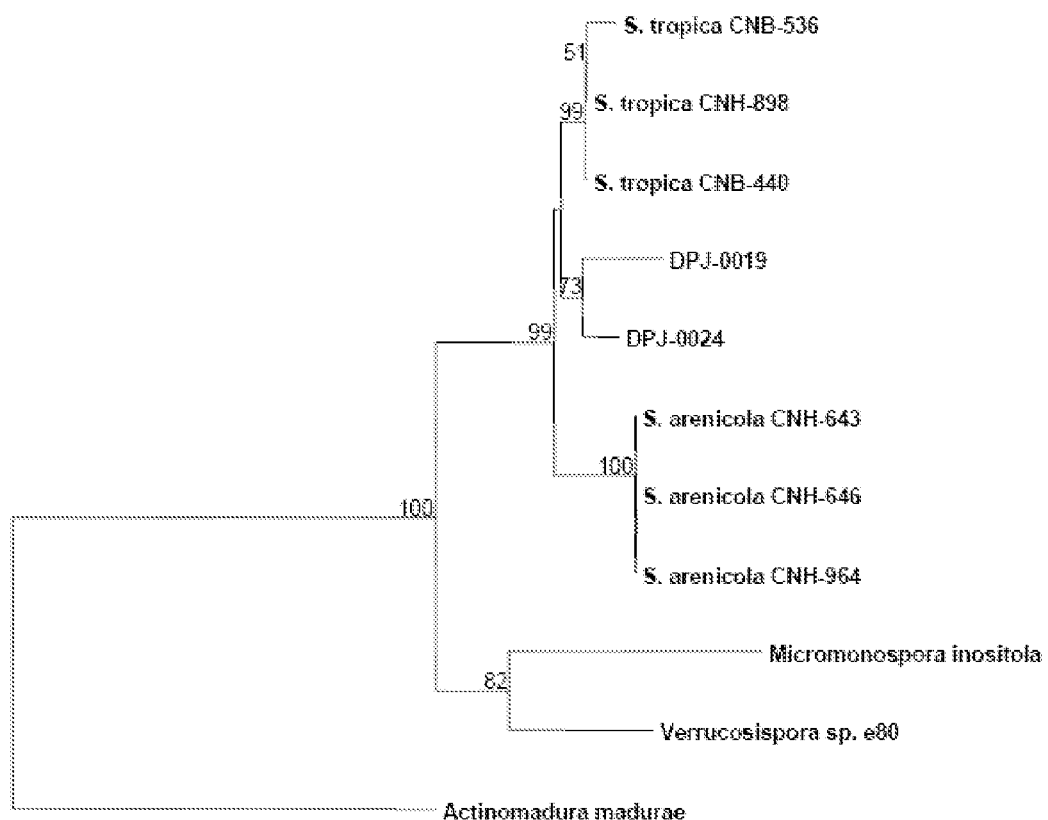
FIG. 2 illustrates the phylogenetic relationships of DPJ-0019 and DPJ-0024 to strains of the two currently accepted *Salinispora* spp., *Salinispora arenicola* and *Salinispora tropica*. The phylogenetic tree was generated with complete 16S-23S intergenic spacer rDNA sequences. A neighbor-joining method was used to calculate distances. Bootstrap values were calculated with 1000 replicates and are shown at their respective nodes if the value is greater than or equal to 50%. *Actinomadura madurae* was used as an outgroup.

Definitions:
"Alkyl" refers to monovalent saturated aliphatic hydrocarbyl groups having from 1 to 6 carbon atoms ($C_1$-$C_6$ alkyl), and preferably 1 to 4 carbon atoms ($C_1$-$C_4$ alkyl). This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), and t-butyl (($CH_3)_3C$—).

"Hydroxy" refers to the group —OH.
"Methoxy" refers to the group —$OCH_3$.
"Stereoisomer" refers to compounds that differ in the chirality or atomic connectivity at one or more stereocenters. Stereoisomers include enantiomers, diastereomers as well as cis-trans (E/Z) isomerism.

At various places in the present specification, substituents of compounds are disclosed in groups or in ranges. It is specifically intended that the description include each and every individual subcombination of the members of such groups and ranges. For example, the term "$C_{1-4}$ alkyl" is specifically intended to individually disclose $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as imidazoles, benzimidazoles, triazoles, and tetrazoles.

"Patient" or "subject" refers to mammals and includes humans and non-human mammals, such as dogs, cats, mice, rats, cows, rabbits and monkeys. Preferably the patient or subject is human.

As used herein, an "isolated" compound is a compound that is either: in substantially pure form, for example, greater than about 95% purity; or not in the presence of or in contact with a wild-type actinomycetes strain. An "isolated" strain indicates a strain that is removed from its natural environment and/or in a growth media for fermentation.

As used herein, the term "fermenting" or "fermentation" of a bacterial strain refers to cultivation of that strain and/or facilitation of biosynthetic production of compounds, such as actinomycetes production of pyrrolo[4,3,2-de]quinolin-8-amine compounds.

A "pyrrolo[4,3,2-de]quinolin-8-amine" compound has the following core structure:

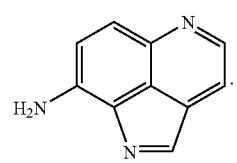

"Pharmaceutically acceptable salt" refers to pharmaceutically acceptable salts of a compound, which salts are derived from a variety of organic and inorganic counter ions well known in the art and include, by way of example only, sodium, aluminum, lithium, zinc, diethanolamine salts, potassium, calcium, magnesium, ammonium, and tetraalkylammonium; and when the molecule contains a basic functionality, salts of organic or inorganic acids, such as, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, besylate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids as well. For a review on pharmaceutically acceptable salts see BERGE ET AL., 66 J. PHARM. SCI. 1-19 (1977), incorporated herein by reference.

The pharmaceutically acceptable salts are prepared by contacting a compound, such as the compound of formula (I) with an acid or salt such as, hydrochloric acid, hydrobromic acid, acetic acid, phosphoric acid, boric acid, perchloric acid, tartaric acid, maleic acid, citric acid, methanesulfonic acid, ascorbic acid, sodium iodide and the like. A solvent employed may be selected from ketones such as acetone, diethyl ketone, methyl ethyl ketone or their mixtures, methanol, ethanol, n-hexane, ethylacetate, benzene, diethylamine, formaldehyde, chloroform, dichloromethane or mixture thereof.

"Treating" or "treatment" of a disease in a subject refers to: inhibiting the disease or arresting its development; ameliorating a symptom of the disease; or causing regression of the disease. Accordingly, "treatment of cancer" as used herein encompasses amelioration of symptoms associated with cancer.

"Modulating mTOR activity" refers to affecting (i.e. inhibition or stimulation) processes or signaling events associated with the mTOR kinase.

Reference to the "absence of sodium" indicates the absence of sodium metal per se or any sodium-containing compound (e.g. sodium chloride).

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

Strain "DPJ-0019" has been assigned Agricultural Research Service Culture Collection (NRRL) Accession No NRRL 50168. Strain "DPJ-0024" has been assigned Agricultural Research Service Culture Collection (NRRL) Accession No NRRL 50167.

One aspect of the invention provides a compound of formula I:

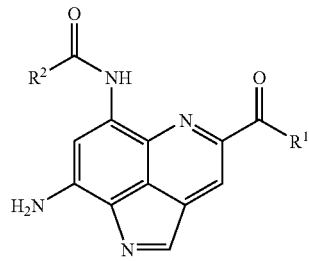

wherein,
$R^1$ is CH=CH—OCH$_3$ or (CH$_2$)$_2$OH; and
$R^2$ is C$_1$-C$_4$ alkyl; or
a tautomer thereof; a stereoisomer thereof; or a pharmaceutically acceptable salt of such compound, stereoisomer or tautomer;
provided that if $R^2$ is methyl, then $R^1$ is (CH$_2$)$_2$OH.

In another embodiment, $R^1$ is CH=CH—OCH$_3$. In another embodiment $R^1$ is CH=CH—OCH$_3$ and $R^2$ is ethyl, isopropyl, isobutyl and sec-butyl. In another embodiment, $R^2$ is C$_2$-C$_4$ alkyl. In another embodiment, $R^1$ is (CH$_2$)$_2$OH. In another embodiment, $R^1$ is (CH$_2$)$_2$OH and $R^2$ is methyl. In another embodiment, $R^1$ is (CH$_2$)$_2$OH and $R^2$ is selected from the group consisting of methyl, ethyl, n-propyl, isopropyl, isobutyl and sec-butyl. In another embodiment, $R^2$ is isopropyl. In another embodiment, $R^1$ is CH=CH—OCH$_3$ and $R^2$ is ethyl or isopropyl. In another embodiment, $R^1$ is (CH$_2$)$_2$OH and $R^2$ is methyl, ethyl, n-propyl, isopropyl, isobutyl or sec-butyl.

Another aspect of the invention provides a compound selected from the group consisting of
(E)-N-(8-amino-4-(3-methoxyacryloyl)pyrrolo[4,3,2-de]quinolin-6-yl)-propionamide;
(E)-N-(8-amino-4-(3-methoxyacryloyl)pyrrolo[4,3,2-de]quinolin-6-yl)isobutyramide;
(E)-N-(8-amino-4-(3-methoxyacryloyl)pyrrolo[4,3,2-de]quinolin-6-yl)-3-methylbutanamide;
(E)-N-(8-amino-4-(3-methoxyacryloyl)pyrrolo[4,3,2-de]quinolin-6-yl)-2-methylbutanamide;
N-(8-amino-4-(3-hydroxypropanoyl)pyrrolo[4,3,2-de]quinolin-6-yl)propionamide;
N-(8-amino-4-(3-hydroxypropanoyl)pyrrolo[4,3,2-de]quinolin-6-yl)isobutyramide;
N-(8-amino-4-(3-hydroxypropanoyl)pyrrolo[4,3,2-de]quinolin-6-yl)-3-methylbutanamide; N-(8-amino-4-(3-hydroxypropanoyl)pyrrolo[4,3,2-de]quinolin-6-yl)-2-methylbutanamide; N-(8-amino-4-(3-hydroxypropanoyl)pyrrolo[4,3,2-de]quinolin-6-yl)acetamide; or
a tautomer thereof; a stereoisomer thereof; or a pharmaceutically acceptable salt of such compound, stereoisomer or tautomer.

Another aspect of the invention provides a pharmaceutical composition comprising a pharmaceutically acceptable carrier and a compound of formula I as described herein; or
a tautomer thereof; a stereoisomer thereof; or a pharmaceutically acceptable salt of such compound, stereoisomer or tautomer.

Another embodiment of the invention provides a composition comprising an isolated compound of formula I as described herein; or a tautomer thereof; a stereoisomer thereof; or a pharmaceutically acceptable salt of such compound, stereoisomer or tautomer.

Another embodiment of the invention provides an isolated actinomycetes strain characterized by an 16S rRNA gene sequence comprising at least 99.9% homology to SEQ ID NO:1; and wherein said actinomycetes strain is capable of growing in the absence of sodium.

Another embodiment of the invention provides an isolated actinomycete having the Agricultural Research Service Culture Collection (NRRL) Accession No NRRL 50168.

Another embodiment of the invention provides a compound of formula I as described herein, a tautomer of the compound, or a pharmaceutically acceptable salt of the compound or tautomer, wherein the compound is produced by an actinomycetes strain having the Agricultural Research Service Culture Collection (NRRL) Accession No NRRL 50168. provided that the compound is not lymphostin. In a more particular embodiment, the compound of formula I is selected from the group consisting of:
E)-N-(8-amino-4-(3-methoxyacryloyl)pyrrolo[4,3,2-de]
  quinolin-6-yl)-propionamide;
(E)-N-(8-amino-4-(3-methoxyacryloyl)pyrrolo[4,3,2-de]
  quinolin-6-yl)isobutyramide;
(E)-N-(8-amino-4-(3-methoxyacryloyl)pyrrolo[4,3,2-de]
  quinolin-6-yl)-3-methylbutanamide;
(E)-N-(8-amino-4-(3-methoxyacryloyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide; and
N-(8-amino-4-(3-hydroxypropanoyl)pyrrolo[4,3,2-de]
  quinolin-6-yl)acetamide; or
a tautomer thereof; a stereoisomer thereof; or a pharmaceutically acceptable salt of such compound, stereoisomer or tautomer.

Another embodiment of the invention provides an isolated actinomycetes strain characterized by an 16S rRNA gene sequence comprising at least 99.9% homology to SEQ ID NO:2;

provided that the 16S rRNA gene sequence comprises SEQ ID NO:3.

Another embodiment of the invention provides an isolated actinomycetes strain having the Agricultural Research Service Culture Collection (NRRL) Accession No NRRL 50167.

Another embodiment of the invention provides an isolated pyrrolo[4,3,2-de]quinolin-8-amine compound, a tautomer of the compound, or a pharmaceutically acceptable salt of the compound or tautomer, wherein the compound is produced by an actinomycetes strain having the Agricultural Research Service Culture Collection (NRRL) Accession No NRRL 50167;

provided that the compound is not lymphostin.

Another embodiment of the invention provides an isolated compound of formula I as described herein, a tautomer of the compound, or a pharmaceutically acceptable salt of the compound or tautomer, wherein the compound is produced by an actinomycetes strain described herein. In a more particular embodiment, the compound of formula I is selected from the group consisting of:
(E)-N-(8-amino-4-(3-methoxyacryloyl)pyrrolo[4,3,2-de]
  quinolin-6-yl)-propionamide;
(E)-N-(8-amino-4-(3-methoxyacryloyl)pyrrolo[4,3,2-de]
  quinolin-6-yl)isobutyramide;
(E)-N-(8-amino-4-(3-methoxyacryloyl)pyrrolo[4,3,2-de]
  quinolin-6-yl)-3-methylbutanamide;
(E)-N-(8-amino-4-(3-methoxyacryloyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide; and
N-(8-amino-4-(3-hydroxypropanoyl)pyrrolo[4,3,2-de]
  quinolin-6-yl)acetamide; or
a tautomer thereof; a stereoisomer thereof; or a pharmaceutically acceptable salt of such compound, stereoisomer or tautomer.

Another embodiment of the invention provides a method of treating a patient suffering from cancer comprising administering an effective amount of a compound of formula I as described herein, or a tautomer or pharmaceutically acceptable salt thereof. In a more particular embodiment, the compound of formula I is selected from the group consisting of:
(E)-N-(8-amino-4-(3-methoxyacryloyl)pyrrolo[4,3,2-de]
  quinolin-6-yl)-propionamide;
(E)-N-(8-amino-4-(3-methoxyacryloyl)pyrrolo[4,3,2-de]
  quinolin-6-yl)isobutyramide;
(E)-N-(8-amino-4-(3-methoxyacryloyl)pyrrolo[4,3,2-de]
  quinolin-6-yl)-3-methylbutanamide;
(E)-N-(8-amino-4-(3-methoxyacryloyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide; and
N-(8-amino-4-(3-hydroxypropanoyl)pyrrolo[4,3,2-de]
  quinolin-6-yl)acetamide; or
a tautomer thereof; a stereoisomer thereof; or a pharmaceutically acceptable salt of such compound, stereoisomer or tautomer.

In another embodiment, the patient is suffering from colon cancer, rectal cancer, gastric cancer, thyroid carcinoma, renal cell carcinoma, cancer of the tongue, bladder carcinoma, cilium carcinoma, hepatoma, prostate cancer, carcinoma uteri, cancer of pharynx, lung cancer, breast cancer, malignant melanoma, granuloma, Kaposi's sarcoma, brain cancer, neuroblastoma, ovarian cancer, testicular cancer, pancreatic cancer, hypernephroma, hemangioendothelioma, adult T-cell leukemia (ATL), chronic myelogenous leukemia (CML), acute myelogenous leukemia (AML) or multiple myeloma.

Another embodiment of the invention provides a method of inhibiting mTOR comprising contacting a cell with a compound of formula I as described herein, a tautomer thereof; a stereoisomer thereof; or a pharmaceutically acceptable salt of such compound, stereoisomer or tautomer.

Another embodiment of the invention provides a method of treating a patient suffering from a condition mediated by mTOR comprising administering a compound of formula I as described herein, a tautomer thereof; a stereoisomer thereof; or a pharmaceutically acceptable salt of such compound, stereoisomer or tautomer.

Another aspect of the invention provides a process for the preparation of a pyrrolo[4,3,2-de]quinolin-8-amine compound comprising:

fermenting an actinomycetes strain having the Agricultural Research Service Culture Collection (NRRL) Accession No NRRL 50168 in a growth medium comprising a salt to form a fermented solution, wherein the pyrrolo[4,3,2-de]quinolin-8-amine compound is formed in the fermented solution; and optionally purifying the pyrrolo[4,3,2-de]quinolin-8-amine compound.

More particularly, the process further comprises extracting the compound from the contacted solution. More particular still, the process further comprises:

centrifuging the fermented solution to form a supernatant and a pellet;

separating the pellet from the supernatant; and extracting the pyrrolo[4,3,2-de]quinolin-8-amine compound from the pellet.

In another aspect of the process, the salt is not sodium chloride (NaCl). More particularly, the salt is potassium chloride (KCl). In another embodiment, the salt is sodium chloride (NaCl). In another embodiment, the process further comprises homogenizing a tissue sample comprising cells from the actinomycetes strain, before the contacting step. In another embodiment, the process further comprises a step of lysing the cells directly after the separating step. In another embodiment, the process further comprises washing the pellet with an aqueous solution before the extracting step. In another embodiment, the extracting step comprises contacting the pellet with an organic solution. In another embodiment, the organic solution comprises ethyl acetate.

A more particular embodiment of the process comprises the purifying step, wherein the purifying comprises high-pressure liquid chromatography (HPLC). More particularly, the purifying step comprises reverse phase HPLC. Alternatively or additionally, the purifying step comprises normal phase HPLC. More particularly, normal phase HPLC is performed on a diol column. More particular still, the normal phase comprises a solvent gradient system comprising about 0% to about 10% isopropanol in a toluene/ethyl acetate mixture. In another embodiment, the reverse phase HPLC is performed on an ODS column. More particularly, the reverse phase comprises acetonitrile and water.

In another embodiment, the, the purifying step comprises normal phase HPLC, performed on a diol column and the compound of is selected from the group consisting of:
N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide; and
N-(8-amino-4-(3-hydroxypropanoyl)pyrrolo[4,3,2-de]
  quinolin-6-yl)acetamide.

In another embodiment, the growth medium further comprises glucose. In another embodiment, the growth medium further comprises a precursor specific to the pyrrolo[4,3,2-de]quinolin-8-amine compound.

Another aspect of the invention provides pyrrolo[4,3,2-de]quinolin-8-amine compound prepared by the process described above, provided that the compound is not lymphostin. In another embodiment, the pyrrolo[4,3,2-de]quinolin-8-amine compound is selected from the group consisting of:
(E)-N-(8-amino-4-(3-methoxyacryloyl)pyrrolo[4,3,2-de]
  quinolin-6-yl)-propionamide;
(E)-N-(8-amino-4-(3-methoxyacryloyl)pyrrolo[4,3,2-de]
  quinolin-6-yl)isobutyramide;
(E)-N-(8-amino-4-(3-methoxyacryloyl)pyrrolo[4,3,2-de]
  quinolin-6-yl)-3-methylbutanamide;
(E)-N-(8-amino-4-(3-methoxyacryloyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)propionamide;
N-(8-amino-4-(3-hydroxypropanoyl)pyrrolo[4,3,2-de]
  quinolin-6-yl)isobutyramide;
N-(8-amino-4-(3-hydroxypropanoyl)pyrrolo[4,3,2-de]
  quinolin-6-yl)-3-methylbutanamide;
N-(8-amino-4-(3-hydroxypropanoyl)pyrrolo[4,3,2-de]
  quinolin-6-yl)-2-methylbutanamide;
N-(8-amino-4-(3-hydroxypropanoyl)pyrrolo[4,3,2-de]
  quinolin-6-yl)acetamide; or
a tautomer thereof; a stereoisomer thereof; or a pharmaceutically acceptable salt of such compound, stereoisomer or tautomer.

Another aspect of the invention provides a process for the preparation of a pyrrolo[4,3,2-de]quinolin-8-amine compound comprising:

contacting cells from ascidian *Didemnum proliferum* with a growth medium comprising a salt to form a contacted solution;

centrifuging the contacted solution to form a supernatant and a pellet;

separating the pellet from the supernatant; and extracting the pyrrolo[4,3,2-de]quinolin-8-amine compound from the pellet.

More particularly, the process further comprises a step of purifying the pyrrolo[4,3,2-de]quinolin-8-amine compound after the extracting step.

The compounds of the present invention may be administered to humans and other animals orally, parenterally, sublingually, by aerosolization or inhalation spray, rectally, intracisternally, intravaginally, intraperitoneally, bucally, intravenously, subcutaneously, intrathecally or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions, which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Effective amounts of the compounds of the invention generally include any amount sufficient to detectably modulate mTOR activity, or by alleviation of symptoms of diseases associated with mTOR activity or susceptible to mTOR activity modulation. An effective dose will generally be a total daily dose administered to a host in single or divided doses and may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose. In general, treatment regimens according to the present invention comprise administration to a patient in need of such treatment from about 10 mg to about 2000 mg of the compound(s) of this invention per day in single or multiple doses.

The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

In another aspect of the invention, kits that include one or more compounds of the invention are provided. Representative kits include a mTOR inhibitor compound of the invention (e.g., a compound of Formula I) and a package insert or other labeling including directions for treating cancer by administering an effective amount of a compound of the present invention.

It is understood that the invention is not limited to the embodiments set forth herein for illustration, but embraces all such forms thereof as come within the scope of the above disclosure.

EXAMPLES

Deposits

Actinomycetes strains DPJ-0019 and DPJ-0024 were deposited on Aug. 14, 2008 with the Agricultural Research Service (ARS) Culture Collection, housed in the Microbial Genomics and Bioprocessing Research Unit of the National Center for Agricultural Utilization Research (NCAUR), under the Budapest Treaty provisions. The address of NCAUR is 1815 N. University Street, Peoria, Ill., 61604. The DPJ-0019 strain was given Patent Deposit No. NRRL 50168. The DPJ-0024 strain was given Patent Deposit No. NRRL 50167.

Example 1

Isolation and Identification of Marine Actinomycete Strain DPJ-0024 and DPJ-0019

Bacterial strains DPJ-0024 and DPJ-0019 were isolated from the ascidian *Didemnum proliferum* Kott collected by SCUBA at Shishijima Island, Japan. From a frozen sample, 120 mg of inner core tissue was macerated in 1 mL of sterile seawater. The resulting homogenized slurry was plated onto two selective media. The plates were examined periodically for the presence of actinomycete colonies. Isolates were transferred to fresh agar media.

Salt dependent growth tests were performed on medium M1 supplemented with different salts, including sodium, potassium, cesium, rubidium, and lithium. For this test, DPJ-0024 and DPJ-0019 strains were grown in liquid medium containing sea salts for 4 days. Mycelia of each strain were harvested, washed three times with 10.3% glucose and re-suspended in the same solution. 10 µL of each strain was spread onto M1 agar plates supplemented with different salts and incubated at 28° C. for four to eight weeks. DPJ-0024 only grew on M1 supplemented with 0.4M or 0.45M NaCl, suggesting it is an obligated sodium-requiring strain. Growth of DPJ-0019 was observed on M1 supplemented with 0.45M KCl, as well as on M1 supplemented with 0.4M or 0.45M NaCl. Further sub-culture of DPJ-0019 colonies from M1 agar with 0.45M KCl confirmed that supplementation of 0.45M KCl is enough to support the growth of DPJ-0019 in solid and liquid M1 medium. These results indicate that DPJ-0019 is not an obligated sodium-requiring strain.

Chromosomal DNA was isolated from an agar-grown culture of DPJ-0024 and DPJ-0019 using lysozyme, SDS cell lysis followed by a phenol/chloroform/isoamyl alcohol precipitation. The almost complete 16S rRNA was PCR amplified using partial primers of 8FPL and 1492RPL. The nearly complete 16S rRNA gene sequence (rDNA) of strain DPJ-0024 shared 99.2% identity with that of *Salinispora arenicola* and 99.4% identity with that of *Salinispora tropica* in the GenBank database (see alignment in FIG. 3). However, DPJ-0024 rDNA does not have adenosine at position 198 (corresponding to analogous position 207 of the *E. coli* 16S rRNA sequence), which is one of the four unique signature nucleotides that were conserved in all currently reported *Salinispora* strains. The 16S rDNA sequence of DPJ-0019 shares 99.2% identity with that of *Salinispora arenicola* and 99.6% identity with that of *Salinispora tropica* in the GenBank database, and has all of the four *Salinispora* signature nucleotides (FIG. 3). The 16S-23S intergenic spacer region rRNA gene sequence of DPJ-0019 and DPJ-0024 were also amplified by using primers 16S-1525F: GGTTGGATCCACCTCCTT (SEQ ID NO:4) and 23S-40R: TCCCACGTCCTTCAT CGG (SEQ ID NO:5). An alignment of the 16S-23S intergenic spacer region rDNA sequences was performed with ClustalX and included several sequences of *Salinispora* species. From the alignment, a phylogram was constructed to demonstrate the phylogenetic relationships. A clear distinction was found between *Salinispora* sp. and the group constituted by DPJ-0019 and DPJ-0024 (FIG. 2).

The results of the physiological growth test, 16S rRNA gene sequences and 16S-23S intergenic spacer rRNA gene sequence comparison reevealed that DPJ-0024 and DPJ-0019 are related to *Salinispora* spp., a recently published genus that displays an obligated requirement of sodium for growth and four unique 16S rRNA signature nucleotides. However, DPJ-0024 is clearly distinguishable from the previously reported *Salinispora* strains based on the fact that it does not have one of the four unique 16S rRNA signature nucleotides (A207). DPJ-0019 has all of the four 16S rRNA signature nucleotides unique for *Salinispora* spp., yet does not have an obligated requirement of sodium for growth. In addition, the 16S-23S internal transcribed spacer sequences of DPJ-0019 and DPJ-0024 clearly indicate that these two strains form a unique group distinguishable from the reported *Salinispora* species. Therefore, DPJ-0019 and DPJ-0024 belong to the family Micromonosporaceae, being taxonomically classified as a group that is closely related to, yet is distinguishable from other *Salinispora* sp.

Example 2

Fermentation of Strain DPJ-0024 and DPJ-0019

Seed Culture:
A loop of agar-grown culture or 20 µL of cryopreserved culture was used to inoculate 7 mL of sterile WSB4YE1/2SS medium and propagated on a rotary shaker at 28° C. and 200 rpm for 72-96 h. WSB4YE1/2SS medium consists of: Glucose 20 g/L, WGE80M (wheat hydrolysate) 5 g/L, SE50MAF (soy hydrolysate) 15 g/L, Yeast Extract 3 g/L, Soluble starch 10 g/L, at pH 7.0.

Fermentation:
After inoculation from a well-grown WSB4YE1/2SS seed culture, strain DPJ-0024 or DPJ-0019 was propagated in 250 mL Erlenmeyer flasks containing 50 mL M48-9 fermentation medium and grown on a rotary shaker at 28° C. and 200 rpm for 7 to 14 days. M48-9 medium consists of soluble starch 30 g/L, molasses 20 g/L, soy peptone 7.5 g/L, yeast extract 2.5 g/L, HP20-10% (w/v), at pH 7.0.

Sample Processing for LCMS Analysis:

2 mL culture broth was centrifuged, supernatant discarded, and the pellet was extracted (mycelia+HP20) with ethyl acetate twice (2 mL each, 4 mL total). The resulting extracts were dried in vacuo, re-dissolved in 200 μL acetonitrile and transferred into small EP tubes. The mixture was centrifuged at highest speed for ~5 min to pellet any precipitates. ~100 μL of clear extract was transferred into a small glass vial with insert for LC/MS.

Example 3

Analytical LCMS Analysis of the Tricyclic Alkaloids Metabolites Produced by DPJ-0019 and DPJ-0024

Samples (2 μL) were analyzed using a model HP1100 Hewlett Packard liquid chromatograph with tandem photodiode array and mass spectral detection. Compounds were resolved on a YMC ODS-A 2.0×100 mm C18 HPLC column using linear gradient from 10 to 50% mobile phase B (0.05% formic acid in acetonitrile) in mobile phase A (0.05% formic acid in water) over 15 minutes. The flow rate was 0.3 ml/min. A total scan UV chromatogram was acquired over a scan range from 210 to 600 nanometers. UV spectra were acquired throughout the run from 210 to 600 nanometers with scan step of 2 nanometers. After emerging from the UV flow cell, the effluent stream entered a Thermo Finnigan DECA ion trap mass spectrometer. The mass spectrometer was fitted with an electrospray ionization (ESI) probe and was operated in alternating positive-ion and negative-ion full scan (150-1500 mass units) mode. The spray needle voltage was set to 4.5 kV for positive and 4.5 kV for negative. The capillary voltages were set at 24 V and −47 V for positive and negative, respectively. The capillary temperature was set to 275° C. Nitrogen was used as the sheath gas which was set to 40 units.

Example 4

General Scheme for the Isolation and Purification of the Tricyclic Alkaloids

Compound numbers 1, 2, 3, 4, 5, 6, 7, 8 and 9 listed in Table 1, as well as lymphostin, were purified from the cultured broth of DPJ-0019. The fermentation culture was centrifuged and the compounds were extracted from the water washed pellet of the fermentation solids using ethyl acetate. The extract was dried under reduced pressure to form a residue which were adsorbed onto silica gel and desorbed with washes consisting of isopropanol:toluene:ethyl acetate, 5:32:63 and 10:30:60. The washes were dried separately to form residues of 5% and 10% concentrated analog mixtures.

The 5% isopropanol residue was composed of compound numbers 1, 2, 3, 4, 5, 8, 9 and lymphostin. Reversed phase High Performance Liquid Chromatography (flow rate 8 ml/min, detection 254 nm) on an ODS column (YMC-Pack ODS A 250×20 mm S-5 μm 120 Å from YMC, Inc.) using acetonitrile in water gradient (20-50% and 10-40% acetonitrile in water gradient) yielded clean compound 1 and 2 and three other fractions containing compound numbers 3, 4, 5, 8 and 9. A second round of reverse phase chromatography on one fraction yielded a mixture of compound numbers 4 and 5. A normal phase HPLC (flow rate: 10 ml/min, detection 460 nm) equipped with a Diol column HPLC (YMC-Diol-120-NP 250×20 mm S-5 μm from YMC, Inc.) using a gradient of isopropanol in a 1:2 mixture of toluene:ethyl acetate (0-10% isopropanol in toluene:ethyl acetate 1:2) on the other two fractions provided pure compound numbers 3 and 9.

The 10% isopropanol fraction was composed of compound numbers 6, 7, 8, 9 and lymphostin as well. After an initial reversed phase HPLC on an ODS column using acetonitrile in water gradient three fractions were generated. Each of these fractions were in turn chromatographed on the Diol column using a gradient of isopropanol in a 1:2 mixture of toluene: ethyl acetate to generate pure compound numbers 6, 7 and 8.

Example 5

Synthesis of Compounds

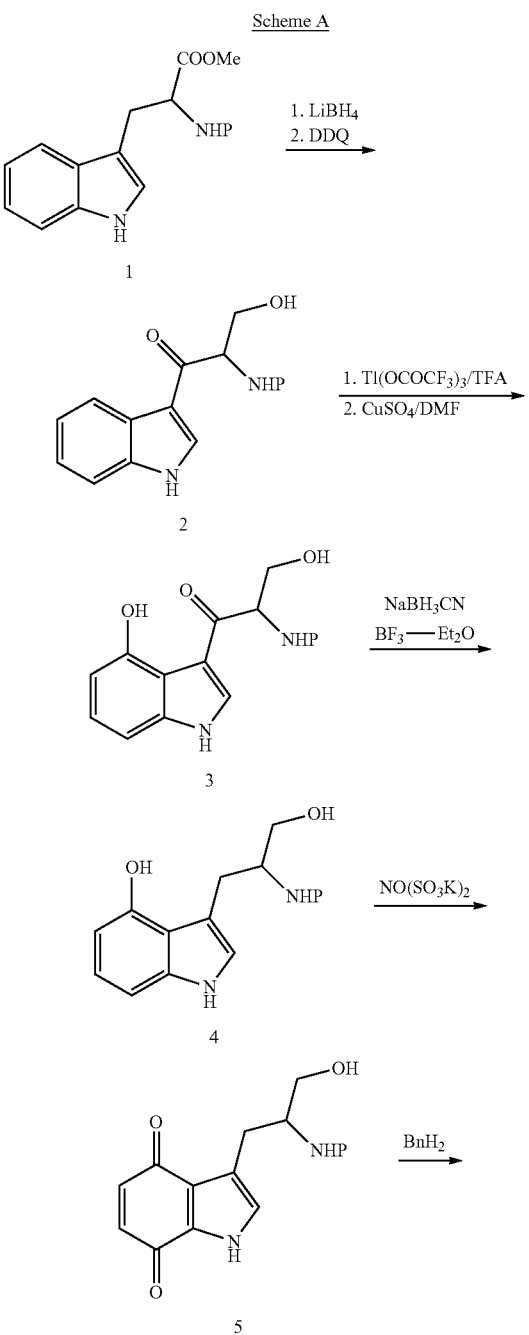

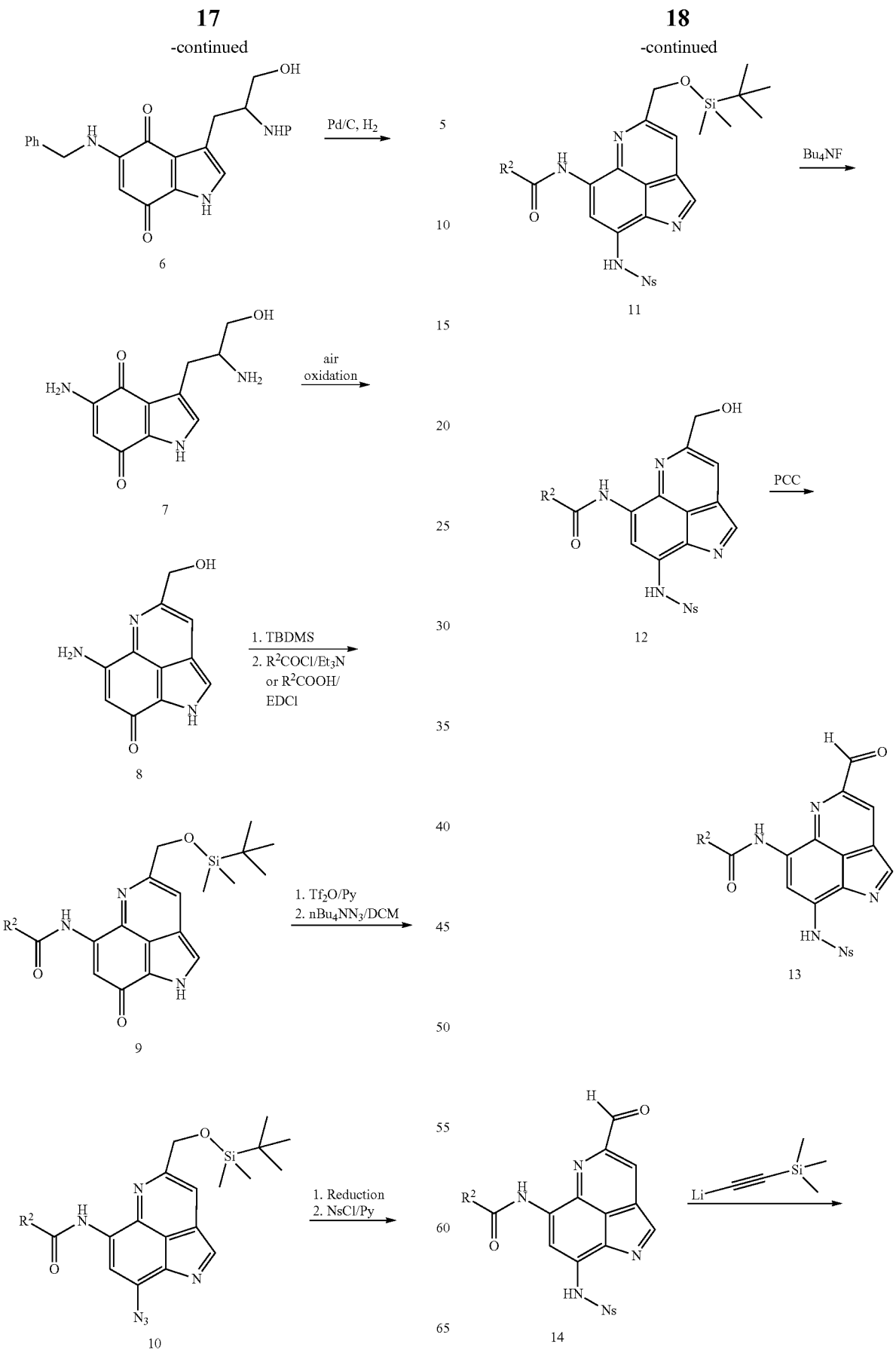

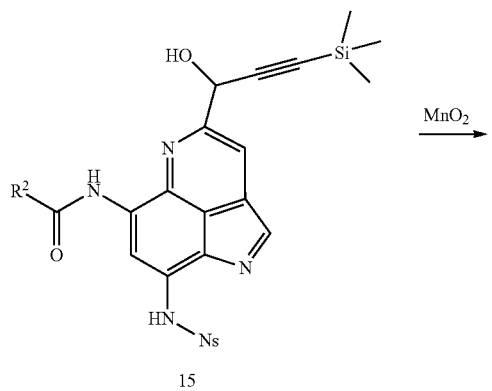

15

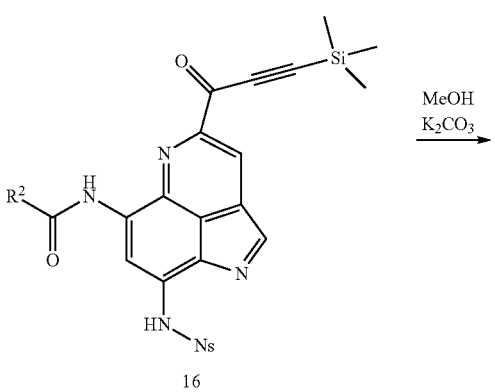

16

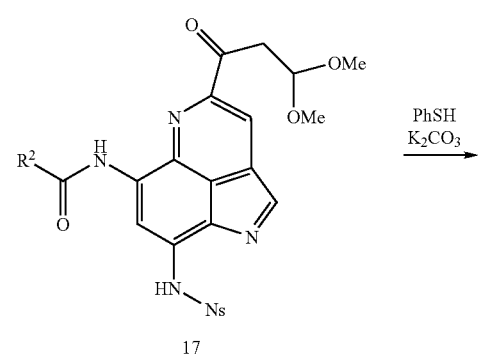

17

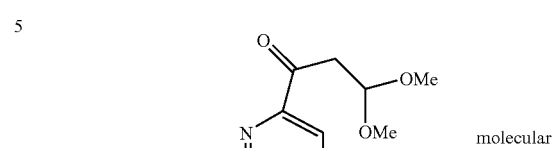

18

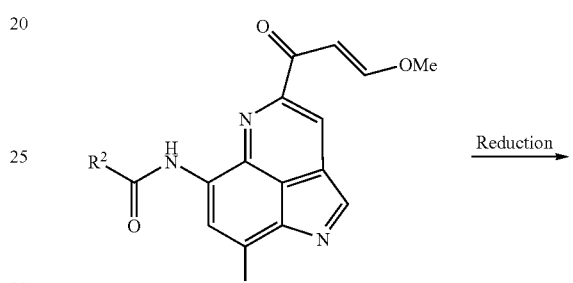

I

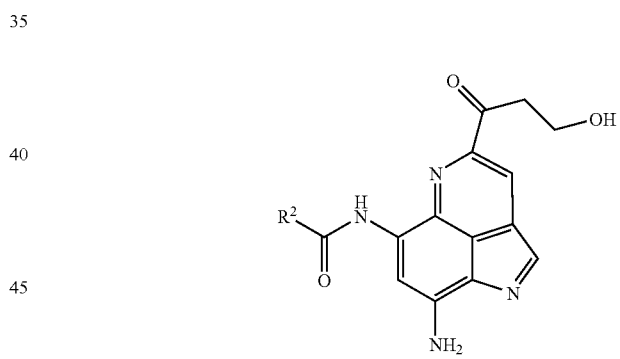

Referring to Scheme A, reduction of the ester moiety of the compound of formula 1, wherein P is a suitable protecting group such as benzyloxy carbonyl (CBz) or t-butoxy carbonyl (BOC), followed by oxidation of the benzylic carbon yields the keto alcohol of formula 2. This reduction can be accomplished using lithium borohydride or another suitable reducing agent such as lithium aluminum hydride in a non-protic solvent such as ether, THF at a temperature from about 0° C. to about 60° C. The benzylic oxidation can be carried out using 2,3-dichloro-5,6-dicyanobenzoquinone (DDQ). Aromatic oxidation of the keto alcohol of formula 2, using an oxidizing agent such as thallium trifluoracetate, followed by treatment with copper sulfate in a solvent such as DMF, will generate the phenol of formula 3.

Reduction of the ketone of formula 3 to form the compound of formula 4, followed by oxidation of the benzo ring of the compound of formula 4 yields the quinone of formula 5. The reduction can be accomplished using sodium cyanoborohydride or another suitable reducing agent such as lithium aluminum hydride or sodium borohydride in a non-protic solvent such as THF or ether at a temperature from about 0° C. to about 60° C. Oxidation of the compound of formula 4 can be accomplished using $(NO(SO_3K)_2)$ (potassium nitrosodisulfanate) in aqueous methanol or acetone under a pH of 6.4-7.0 at room temperature.

Selective introduction of an amine to the aromatic group of the compound of formula 5 to form the compound of formula 6, and the subsequent deprotection of both amino groups of the resulting compound of formula 6 yields the diamino quinine of formula 7. Introduction of the amine can be accomplished via the addition of benzyl amine. This reaction is typically carried out in a non-protic solvent such as THF, pyridine at a temperature from about 0° C. to about 60° C. The two protected amino groups of the resulting compound of formula 6 can be deprotected via reaction with hydrogen gas under standard hydrogenation conditions that are well known to those of skill in the art, for example, in the presence of palladium on carbon, at a pressure of about 1-3 atmospheres and a temperature from about 20° C. to about 80° C. The resulting diamino quinine of formula 7 can then converted into the tricyclic alcohol of formula 8 by subjecting it to reaction with oxygen or oxygen enriched air at a temperature from about 0° C. to about 80° C.

The primary alcohol group of the compound of formula 8 can be selectively protected using an appropriate reagent such as tert-butyldimethylchlorosilane (TBDMSCl) or tert-butyldimethylsilyl (TBDMS) triflate, or another suitable silylating agent, rendering the free amino group available for further derivatization. This reaction can be carried out in a non-aqueous solvent such as dichloromethane or THF, at a temperature from about 0° C. to about 60° C. Acylation of the free amino group can be accomplished using an acylating reagent such as a carboxylic acid or acid chloride. Suitable solvents for this reaction include dichloromethane or THF in the case of acid chlorides and polar solvent such as DMF or NMP in the case of coupling reactions using acids. The temperature can range from about 0° C. to about 60° C. An appropriate coupling reagent such as 1-ethyl-3-(3'-dimethylaminopropyl)carbodiimide (EDCI) or Dicyclohexyl diimide (DCC) yields a compound of formula 9 wherein $R^2$ is $(C_1-C_4)$ alkyl. The compound of formula 9 can be converted into the azide of formula 10 by reaction with triflic anhydride in pyridine, followed by reaction with tetrabutylammonium azide ($nBU_4NN_3$) or sodium azide in solvents such as dichloromethane or THF. Reduction of the azide of formula 10 to give the corresponding amino compound, followed by protection of the amino group with any of a number of protecting groups such as nosyl, Boc and tosyl, using methods well known to those of skill in the art yields the corresponding compound of formula 11. The azide reduction can be carried out using lithium aluminum hydride or another suitable reducing agent well known to those of skill in the art, in a non-aqueous solvent such as THF at a temperature from about 0° C. to about 60° C.

The protected primary alcohol of formula 11 can be deprotected using a reagent containing a fluoride source such as tetrabutyl ammonium fluoride or hydrogen fluoride in a solvent such as THF or using a mineral acid such as hydrochloric acid at a temperature from about 0° C. to about 60° C., to produce the alcohol of formula 12. Oxidation of the alcohol of formula 12, using a reagent such as pyridinium chlorochromate (PCC) or chromium trioxide in a solvent such as dichloromethane or pyridine, at a temperature from about 0° C. to about 60° C., yields the corresponding compound of formula 13.

Reaction of the compound of formula 13 with an appropriately protected lithium ethynyl compound in a non-protic solvent such as ether or THF, at a temperature from about −78° C. to about 60° C., yields the corresponding ethynyl alcohol of formula 15, which can then be oxidized to form the ethynyl ketone of formula 16. The oxidation can be carried out using manganese dioxide or another suitable oxidizing agent such as PCC in a solvent such as acetone or dichloromethane, at a temperature from about 0° C. to about 60° C.

The ethynyl ketone of formula 16 can be converted into the corresponding compound of formula 17 via reaction with methanol under basic conditions, for example, in the presence of potassium carbonate or another suitable base. Suitable solvents for this reaction include methanol. Suitable temperatures range from about 0° C. to about 60° C. Deprotection of the resulting compound of formula 17, using methods well known to those of skill in the art, will yield the acetal of formula 18, which can then be converted into the desired compound of formula I by subjecting it to a dehydrating agent such as molecular sieves.

Further reduction of Formula 1 can be carried out using catalytic hydrogenation using a reagent like Pd/C or Pt/C and hydrogen gas in a solvent such as methanol or using a hydride source such as lithium aluminum hydride in a solvent such as THF or ether.

Example 6 mTOR Kinase Assay

The routine human TOR assays with purified enzyme were performed in 96-well plates by DELFIA format as follows. Enzymes were first diluted in kinase assay buffer (10 mM Hepes (pH 7.4), 50 mM NaCl, 50 mM β-glycerophosphate, 10 mM $MnCl_2$, 0.5 mM DTT, 0.25 μM microcystin LR, and 100 μg/mL BSA). To each well, 12 μL of the diluted enzyme were mixed briefly with 0.5 μL test inhibitor or control vehicle dimethylsulfoxide (DMSO). The kinase reaction was initiated by adding 12.5 μL kinase assay buffer containing ATP and His6-S6K to give a final reaction volume of 25 μL containing 800 ng/mL FLAG-TOR, 100 μM ATP and 1.25 μM His6-S6K. The reaction plate was incubated for 2 hours (linear at 1-6 hours) at room temperature with gentle shaking and then terminated by adding 25 μL Stop buffer (20 mM Hepes (pH 7.4), 20 mM EDTA, 20 mM EGTA). The DELFIA detection of the phosphorylated (Thr-389) His6-S6K was performed at room temperature using a monoclonal anti-P (T389)-p70S6K antibody (1A5, Cell Signaling) labeled with Europium-N1-ITC (Eu) (10.4 Eu per antibody, PerkinElmer). The DELFIA Assay buffer and Enhancement solution were purchased from PerkinElmer. 45 μL of the terminated kinase reaction mixture was transferred to a MaxiSorp plate (Nunc) containing 55 μL PBS. The His6-S6K was allowed to attach for 2 hours after which the wells were aspirated and washed once with PBS. 100 μL of DELFIA Assay buffer with 40 ng/mL Eu-P(T389)—S6K antibody was added. The antibody binding was continued for 1 hour with gentle agitation. The wells were then aspirated and washed 4 times with PBS containing 0.05% Tween-20 (PBST). 100 μL of DELFIA Enhancement solution was added to each well and the plates were read in a PerkinElmer Victor model plate reader. Data obtained were used to calculate enzymatic activity and enzyme inhibition by potential inhibitors. mTOR $IC_{50}$ data (reported in μM) is provided in Table 1.

TABLE 1

| Cmpd. No. | Structure | Name | mTOR IC$_{50}$ (μM) | LNCap IC50 (μM) | MDA 468 IC50 (μM) | RT (min) | m+ ion | m− ion |
|---|---|---|---|---|---|---|---|---|
| 1 | 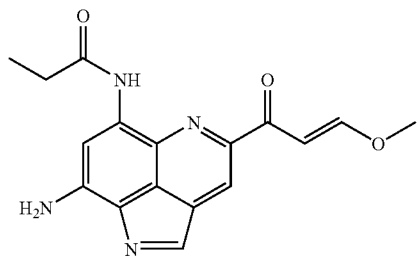 [SMILES: CCC(=O)Nc1cc(N)c2c3c(cc(C(=O)/C=C/OC)nc13)C=N2] | (E)-N-(8-amino-4-(3-methoxyacryloyl)pyrrolo[4,3,2-de]quinolin-6-yl)-propionamide | 0.0015 | 0.048 | 0.085 | 11.60 | 325.1 | 323.3 |
| 2 | 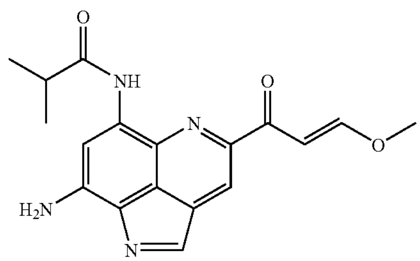 [SMILES: CO/C=C/C(=O)c1cc2c3c(c(N)cc(NC(=O)C(C)C)c3n1)N=C2] | (E)-N-(8-amino-4-(3-methoxyacryloyl)pyrrolo[4,3,2-de]quinolin-6-yl)isobutyramide | 0.0008 | 0.022 | 0.058 | 13.01 | 339.1 | 337.2 |
| 3 | 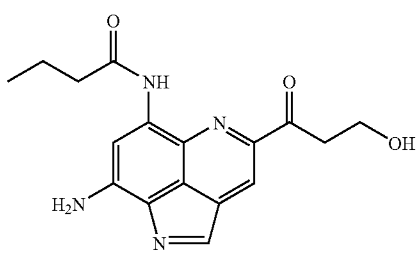 [SMILES: CCCC(=O)Nc1cc(N)c2c3c(cc(C(=O)CCO)nc13)C=N2] | N-(8-amino-4-(3-hydroxypropanoyl)pyrrolo[4,3,2-de]quinolin-6-yl)butyramide | >4 | >12 | >12 | 9.27 | 327.1 | 325.2 |
| 4 | 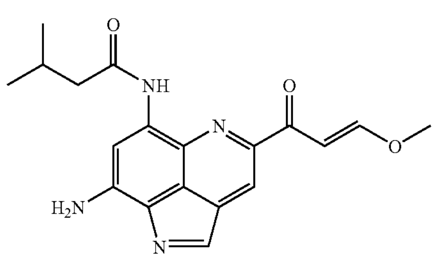 [SMILES: CO/C=C/C(=O)c1cc2c3c(c(N)cc(NC(=O)CC(C)C)c3n1)N=C2] | (E)-N-(8-amino-4-(3-methoxyacryloyl)pyrrolo[4,3,2-de]quinolin-6-yl)-3-methylbutanamide | 0.0018* | 0.23* | 0.7* | 14.41* | 353.2* | 351.3* |
| 5 | 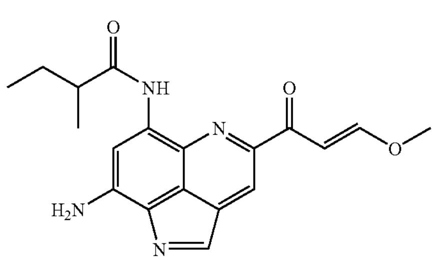 [SMILES: CCC(C)C(=O)Nc1cc(N)c2c3c(cc(C(=O)/C=C/OC)nc13)C=N2] | (E)-N-(8-amino-4-(3-methoxyacryloyl)pyrrolo[4,3,2-de]quinolin-6-yl)-2-methylbutanamide | 0.0018* | 0.23* | 0.7* | 14.41* | 353.2* | 351.3* |

TABLE 1-continued

| Cmpd. No. | Structure | Name | mTOR IC$_{50}$ (µM) | LNCap IC50 (µM) | MDA 468 IC50 (µM) | RT (min) | m+ ion | m− ion |
|---|---|---|---|---|---|---|---|---|
| 6 | 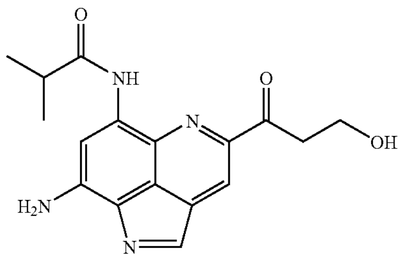 [SMILES: CC(C)C(=O)Nc1cc(N)c2c3c(cc(C(=O)CCO)nc13)C=N2] | N-(8-amino-4-(3-hydroxypropanoyl)pyrrolo[4,3,2-de]quinolin-6-yl)isobutyramide | >4 | 6.5 | 1.2 | 8.86 | 327.1 | 325.3 |
| 7 | 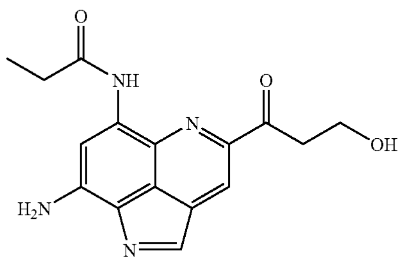 [SMILES: CCC(=O)Nc1cc(N)c2c3c(cc(C(=O)CCO)nc13)C=N2] | N-(8-amino-4-(3-hydroxypropanoyl)pyrrolo[4,3,2-de]quinolin-6-yl)propionamide | >4 | 5 | 0.4 | 7.73 | 313.1 | 311.4 |
| 8 | 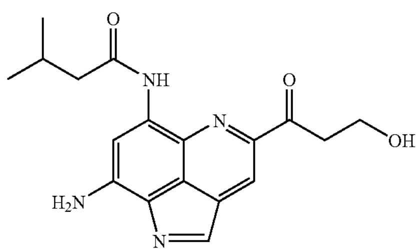 [SMILES: CC(C)CC(=O)Nc1cc(N)c2c3c(cc(C(=O)CCO)nc13)C=N2] | N-(8-amino-4-(3-hydroxypropanoyl)pyrrolo[4,3,2-de]quinolin-6-yl)-3-methylbutanamide | 1.5 | 2.9 | 3.5 | 10.10 | 341.1 | 339.4 |
| 9 | 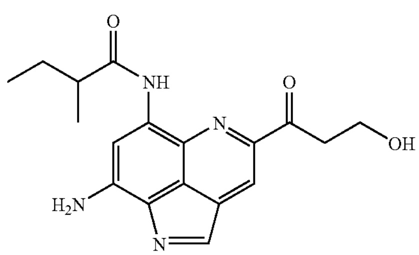 [SMILES: CCC(C)C(=O)Nc1cc(N)c2c3c(cc(C(=O)CCO)nc13)C=N2] | N-(8-amino-4-(3-hydroxypropanoyl)pyrrolo[4,3,2-de]quinolin-6-yl)-2-methylbutanamide | 3.2 | 10 | 7.6 | 10.38 | 341.2 | 339.3 |

*Compounds 4 and 5 were screened as a mixture in the same solution.

Example 7

In Vitro Cell Growth Assay

Cells of human tumor lines LNCap and MDA468 were plated in 96-well culture plates at approximately 3000 cells per well. One day following plating, various doses of mTOR inhibitors were added to cells. Three days after drug treatment, viable cell densities were determined by metabolic conversion (by viable cells) of the dye MTS, a well-established cell proliferation assay. The assays were performed using an assay kit purchased from Promega Corp. (Madison, Wis.) following the protocol supplied with the kit. The MTS assay results were read in a 96-well plate reader by measuring absorbance at 490 nm. The effect of each treatment was calculated as percent of control growth relative to the vehicle-treated cells grown in the same culture plate. The drug concentration that conferred 50% inhibition of growth was determined as IC$_{50}$ (µM). Compounds in Table 1 were screened and compounds 1, 2 and 4 exhibited LNCap IC$_{50}$ ranging from 20 to 300 nM.

Example 8

Tumor Cell mTOR Inhibition Assay

Human cancer cells (LNCap prostate, U87MG glioma) were plated in 6-well plates in growth media for overnight. Cells were treated with various doses of mTOR inhibitors for 6 hours. Total cellular lysates were prepared using NuPAGE-LDS sample buffer (Invitrogen), sonicated and then clarified by centrifugation. Equal amounts of proteins were subject to immunoblotting analysis using NuPAGE electrophoresis system and probed with phospho-specific antibodies against mTOR pathway markers such as AKT, S6K1, 4EBP1. Compounds in Table 1 were screened and compounds 1, 2 and 4 exhibited MDA468 IC$_{50}$ ranging from 50 to 800 nM.

The invention claimed is:

1. The compound (E)-N-(8-amino-4-(3-methoxyacryloyl)pyrrolo[4,3,2-de]quinolin-6-yl)isobutyramide, or a tautomer, stereoisomer or pharmaceutically acceptable salt thereof.

2. A pharmaceutical composition comprising the compound of claim 1 or a tautomer, stereoisomer or pharmaceutically acceptable salt thereof, and a pharmaceutically acceptable carrier.

3. The pharmaceutical composition of claim 2, wherein said compound, tautomer, stereoisomer or pharmaceutically acceptable salt thereof is present in sufficient amount to treat prostate cancer or breast cancer in an patient.

* * * * *

SEQUENCE LISTING

<160> NUMBER OF SEQ ID NOS: 7

<210> SEQ ID NO 1
<211> LENGTH: 1449
<212> TYPE: DNA
<213> ORGANISM: Actinomycete DPJ-0019

<400> SEQUENCE: 1

| | | | | | |
|---|---|---|---|---|---|
| ctcaggacga | acgctggcgg | cgtgcttaac | acatgcaagt | cgagcggaaa | ggcccttcgg | 60 |
| ggtactcgag | cggcgaacgg | gtgagtaaca | cgtgagtaac | ctgccctagg | ctttgggata | 120 |
| accccgggaa | accggggcta | ataccgaata | tgactggctg | ccgcatggtg | gttggtggaa | 180 |
| agattttttcg | gcttgggatg | gactcgcggc | ctatcagctt | gttggtgggg | taatggccta | 240 |
| ccaaggcggc | gacgggtagc | cggcctgaga | gggcgaccgg | ccacactggg | actgagacac | 300 |
| ggcccagact | cctacgggag | gcagcagtgg | ggaatcttgc | acaatgggcg | aaagcctgat | 360 |
| gcagcgacgc | cgcgtgaggg | atgacggcct | tcggttgta | aacctctttc | agcagggacg | 420 |
| aagcgtttgt | gacggtacct | gcagaagaag | cgccggccaa | ctacgtgcca | gcagccgcgg | 480 |
| taagacgtag | ggcgcaagcg | ttgtccggat | ttattgggcg | taaagagctc | gtaggcggct | 540 |
| tgtcgcgtcg | actgtgaaaa | cccgtggctc | aactgcgggc | ttgcagtcga | tacgggcagg | 600 |
| ctagagttcg | gtaggggaga | ctggaattcc | tggtgtagcg | gtgaaatgcg | cagatatcag | 660 |
| gaggaacacc | ggtggcgaag | gcgggtctct | gggccgatac | tgacgctgag | gagcgaaagc | 720 |
| gtggggagcg | aacaggatta | gataccctgg | tagtccacgc | tgtaaacgtt | gggcgctagg | 780 |
| tgtgggggc | ctctccggtt | ctctgtgccg | cagctaacgc | attaagcgcc | ccgcctgggg | 840 |
| agtacggccg | caaggctaaa | actcaaagga | attgacgggg | gcccgcacaa | gcggcggagc | 900 |
| atgcggatta | attcgatgca | acgcgaagaa | ccttacctgg | gtttgacatc | gccgaaaatc | 960 |
| cttcagagat | gggggggtcct | tcggggccgg | tgacaggtgg | tgcatggctg | tcgtcagctc | 1020 |
| gtgtcgtgag | atgttgggtt | aagtcccgca | acgagcgcaa | cccttgttcg | atgttgccag | 1080 |
| cgcgttatgg | cggggactca | tcgaagactg | ccggggtcaa | ctcggaggaa | ggtggggatg | 1140 |
| acgtcaagtc | atcatgcccc | ttatgtccag | ggcttcacgc | atgctacaat | ggccggtaca | 1200 |
| atgggctgcg | ataccgtgag | gtggagcgaa | tcccaaaaag | ccggtctcag | ttcggatcgg | 1260 |
| ggtctgcaac | tcgaccccgt | gaagtcggag | tcgctagtaa | tcgcagatca | gcaacgctgc | 1320 |
| ggtgaatacg | ttcccgggcc | ttgtacacac | cgcccgtcac | gtcacgaaag | tcggcaacac | 1380 |
| ccgaagccgg | tggcctaacc | cttgtggggg | gagccgtcga | aggtggggct | ggcgattggg | 1440 |
| acgaagtcg | | | | | | 1449 |

<210> SEQ ID NO 2
<211> LENGTH: 1447
<212> TYPE: DNA
<213> ORGANISM: Actinomycete DPJ-0024

<400> SEQUENCE: 2

| | | | | | |
|---|---|---|---|---|---|
| gctcaggacg | aacgctggcg | gcgtgcttaa | cacatgcaag | tcgagcggaa | aggcccttcg | 60 |
| gggtactcga | gcggcgaacg | ggtgagtaac | acgtgagtaa | cctgccccag | ctttgggat | 120 |
| aaccccggga | aaccggggct | aataccgaat | attaccggct | gccgcatggc | ggttggtgga | 180 |
| aagtttttcg | gcttgggatg | gactcgcggc | ctatcagctt | gttggtgggg | taatggccta | 240 |
| ccaaggcggc | gacgggtagc | cggcctgaga | gggcgaccgg | ccacactggg | actgagacac | 300 |

| | |
|---|---|
| ggcccagact cctacgggag gcagcagtgg ggaatcttgc acaatgggcg gaagcctgat | 360 |
| gcagcgacgc cgcgtgaggg atgacggcct tcgggttgta aacctctttc agcagggacg | 420 |
| aagcgtttgt gacggtacct gcagaagaag cgccggccaa ctacgtgcca gcagccgcgg | 480 |
| taagacgtag ggcgcgagcg ttgtccggat ttattgggcg taaagagctc gtaggcggct | 540 |
| tgtcgcgtcg actgtgaaaa cccgtggctc aactgcgggc ttgcagtcga tacgggcagg | 600 |
| ctagagttcg gtaggggaga ctggaattcc tggtgtagcg gtgaaatgcg cagatatcag | 660 |
| gaggaacacc ggtggcgaag gcgggtctct gggccgatac tgacgctgag gagcgaaagc | 720 |
| gtggggagcg aacaggatta gatacctggg tagtccacgc tgtaaacgtt gggcgctagg | 780 |
| tgtgggggc ctctccggtt tctgtgccg cagctaacgc attaagcgcc cgcctgggg | 840 |
| agtacggccg caaggctaaa actcaaagga attgacgggg gcccgcacaa gcggcggagc | 900 |
| atgcggatta attcgatgca acgcgaagaa ccttacctgg gtttgacatc gccggaaatc | 960 |
| cttcagagat gggggtcct tcggggccgg tgacaggtgg tgcatggctg tcgtcagctc | 1020 |
| gtgtcgtgag atgttgggtt aagtcccgca acgagcgcaa cccttgttcg atgttgccag | 1080 |
| cgcgttatgg cggggactca tcgaagactg ccggggtcaa ctcggaggaa ggtgggatg | 1140 |
| acgtcaagtc atcatgcccc ttatgtccag ggcttcacgc atgctacaat ggccggtaca | 1200 |
| atgggctgcg ataccgtgag gtggagcgaa tcccaaaaag ccggtctcag ttcggatcgg | 1260 |
| ggtctgcaac tcgaccccgt gaagtcggag tcgctagtaa tcgcagatca gcaacgctgc | 1320 |
| ggtgaatacg ttcccgggcc ttgtacacac cgcccgtcac gtcacgaaag tcggcaacac | 1380 |
| ccgaagccgg tggcctaacc cttgtggggg gagccgtcga aggtggggct ggcgattggg | 1440 |
| acgaagt | 1447 |

```
<210> SEQ ID NO 3
<211> LENGTH: 20
<212> TYPE: DNA
<213> ORGANISM: Artificial
<220> FEATURE:
<223> OTHER INFORMATION: Conserved Domain

<400> SEQUENCE: 3
```

| | |
|---|---|
| cggttggtgg aaagtttttc | 20 |

```
<210> SEQ ID NO 4
<211> LENGTH: 18
<212> TYPE: DNA
<213> ORGANISM: Artificial
<220> FEATURE:
<223> OTHER INFORMATION: primer 16S-1525F

<400> SEQUENCE: 4
```

| | |
|---|---|
| ggttggatcc acctcctt | 18 |

```
<210> SEQ ID NO 5
<211> LENGTH: 18
<212> TYPE: DNA
<213> ORGANISM: Artificial
<220> FEATURE:
<223> OTHER INFORMATION: Primer 23S-40R

<400> SEQUENCE: 5
```

| | |
|---|---|
| tcccacgtcc ttcatcgg | 18 |

```
<210> SEQ ID NO 6
<211> LENGTH: 1479
<212> TYPE: DNA
```

<213> ORGANISM: Streptomyces sp.

<400> SEQUENCE: 6

| | | | | | |
|---|---|---|---|---|---|
| agagtttgat | cctggctcag | gacgaacgct | ggcggcgtgc | ttaacacatg caagtcgagc | 60 |
| ggaaaggccc | ttcggggtac | tcgagcggcg | aacgggtgag | taacacgtga gtaacctgcc | 120 |
| ccaggctttg | gataacccc | gggaaaccgg | ggctaatacc | ggatatgacc atctgtcgca | 180 |
| tggtgggtgg | tggaaagatt | ttttggcttg | ggatgggctc | gcggcctatc agcttgttgg | 240 |
| tggggtgatg | gcctaccaag | gcggcgacgg | gtagccggcc | tgagagggcg accggccaca | 300 |
| ctgggactga | gacacggccc | agactcctac | gggaggcagc | agtggggaat cttgcacaat | 360 |
| gggcggaagc | ctgatgcagc | gacgccgcgt | gagggatgac | ggccttcggg ttgtaaacct | 420 |
| ctttcagcag | ggacgaagcg | tttgtgacgg | tacctgcaga | agaagcgccg gccaactacg | 480 |
| tgccagcagc | cgcggtaaga | cgtagggcgc | aagcgttgtc | cggatttatt gggcgtaaag | 540 |
| agctcgtagg | cggcttgtcg | cgtcgactgt | gaaaacccgt | ggctcaactg cgggcttgca | 600 |
| gtcgatacgg | gcaggctaga | gttcggtagg | ggagactgga | attcctggtg tagcggtgaa | 660 |
| atgcgcagat | atcaggagga | acaccggtgg | cgaaggcggg | tctctgggcc gatactgacg | 720 |
| ctgaggagcg | aaagcgtggg | gagcgaacag | gattagatac | cctggtagtc cacgctgtaa | 780 |
| acgttgggcg | ctaggtgtgg | ggggcctctc | cggttctctg | tgccgcagct aacgcattaa | 840 |
| gcgccccgcc | tggggagtac | ggccgcaagg | ctaaaactca | aaggaattga cggggggcccg | 900 |
| cacaagcggc | ggagcatgcg | gattaattcg | atgcaacgcg | aagaaccttta cctgggtttg | 960 |
| acatcgccgg | aaatccttca | gagatggggg | gtccttcggg | gccggtgaca ggtggtgcat | 1020 |
| ggctgtcgtc | agctcgtgtc | gtgagatgtt | gggttaagtc | ccgcaacgag cgcaaccctt | 1080 |
| gttcgatgtt | gccagcgcgt | tatggcgggg | actcatcgaa | gactgccggg gtcaactcgg | 1140 |
| aggaaggtgg | ggatgacgtc | aagtcatcat | gccccttatg | tccagggctt cacgcatgct | 1200 |
| acaatggccg | gtacagtggg | ctgcgatacc | gtgaggtgga | gcgaatccca aaaagccggt | 1260 |
| ctcagttcgg | atcggggtct | gcaactcgac | cccgtgaagt | cggagtcgct agtaatcgca | 1320 |
| gatcagcaac | gctgcggtga | atacgttccc | gggccttgta | cacaccgccc gtcacgtcac | 1380 |
| gaaagtcggc | aacacccgaa | gccggtggcc | taaccttgt | ggggggagcc gtcgaaggtg | 1440 |
| gggctggcga | ttgggacgaa | gtcgtaacaa | ggtagccgt | | 1479 |

<210> SEQ ID NO 7
<211> LENGTH: 1479
<212> TYPE: DNA
<213> ORGANISM: Streptomyces sp.

<400> SEQUENCE: 7

| | | | | | |
|---|---|---|---|---|---|
| agagtttgat | cctggctcag | gacgaacgct | ggcggcgtgc | ttaacacatg caagtcgagc | 60 |
| ggaaaggccc | ttcggggtac | tcgagcggcg | aacgggtgag | taacacgtga gtaacctgcc | 120 |
| ccaggctttg | gataacccc | gggaaaccgg | ggctaatacc | ggatatgact ggctgccgca | 180 |
| tggtggttgg | tggaaagatt | ttttggcttg | ggatgggctc | gcggcctatc agcttgttgg | 240 |
| tggggtgatg | gcctaccaag | gcggcgacgg | gtagccggcc | tgagagggcg accggccaca | 300 |
| ctgggactga | gacacggccc | agactcctac | gggaggcagc | agtggggaat cttgcacaat | 360 |
| gggcggaagc | ctgatgcagc | gacgccgcgt | gagggatgac | ggccttcggg ttgtaaacct | 420 |
| ctttcagcag | ggacgaagcg | tttgtgacgg | tacctgcaga | agaagcgccg gccaactacg | 480 |
| tgccagcagc | cgcggtaaga | cgtagggcgc | aagcgttgtc | cggatttatt gggcgtaaag | 540 |

```
agctcgtagg cggcttgtcg cgtcgactgt gaaaacccgt ggctcaactg cgggcttgca      600
gtcgatacgg gcaggctaga gttcggtagg ggagactgga attcctggtg tagcggtgaa      660
atgcgcagat atcaggagga acaccggtgg cgaaggcggg tctctgggcc gatactgacg      720
ctgaggagcg aaagcgtggg gagcgaacag gattagatac cctggtagtc cacgctgtaa      780
acgttgggcg ctaggtgtgg ggagcctctc cggttctctg tgccgcagct aacgcattaa      840
gcgccccgcc tggggagtac ggccgcaagg ctaaaactca aaggaattga cgggggcccg      900
cacaagcggc ggagcatgcg gattaattcg atgcaacgcg aagaacctta cctgggtttg      960
acatcgccgg aaatccttca gagatggggg gtccttcggg gccggtgaca ggtggtgcat     1020
ggctgtcgtc agctcgtgtc gtgagatgtt gggttaagtc ccgcaacgag cgcaaccctt     1080
gttcgatgtt gccagcgcgt tatggcgggg actcatcgaa gactgccggg gtcaactcgg     1140
aggaaggtgg ggatgacgtc aagtcatcat gccccttatg tccagggctt cacgcatgct     1200 acaatgccg gtacaatggg ctgcgatacc gtgaggtgga gcgaatccca aaaagccggt     1260
ctcagttcgg atcggggtct gcaactcgac cccgtgaagt cggagtcgct agtaatcgca     1320
gatcagcaac gctgcggtga atacgttccc gggccttgta cacccgccc gtcacgtcac     1380 gaaagtcggc aacacccgaa gccggtggcc taacccttgt ggggggagcc gtcgaaggtg     1440
gggctggcga ttgggacgaa gtcgtaacaa ggtagccgt                             1479
```